US012741958B2

(12) United States Patent
Zhao et al.

(10) Patent No.: US 12,741,958 B2
(45) Date of Patent: Sep. 22, 2026

(54) CRYSTAL FORM OF PYRIMIDINE DERIVATIVE AND PREPARATION METHOD THEREFOR

(71) Applicant: ZHEJIANG HISUN PHARMACEUTICAL CO., LTD., Taizhou (CN)

(72) Inventors: Meiyu Zhao, Taizhou (CN); Lianwei Chen, Taizhou (CN); Na Li, Taizhou (CN); Zhenjuan Shi, Taizhou (CN); Jianfeng Zheng, Taizhou (CN); Di Su, Taizhou (CN)

(73) Assignee: ZHEJIANG HISUN PHARMACEUTICAL CO., LTD., Taizhou (CN)

( * ) Notice: Subject to any disclaimer, the term of this patent is extended or adjusted under 35 U.S.C. 154(b) by 358 days.

(21) Appl. No.: 18/571,216

(22) PCT Filed: Jun. 21, 2022

(86) PCT No.: PCT/CN2022/100065
§ 371 (c)(1),
(2) Date: Dec. 16, 2023

(87) PCT Pub. No.: WO2022/268063
PCT Pub. Date: Dec. 29, 2022

(65) Prior Publication Data

US 2024/0287045 A1 Aug. 29, 2024

(30) Foreign Application Priority Data

Jun. 23, 2021 (CN) ........................ 202110696953.6

(51) Int. Cl.
*C07D 403/12* (2006.01)
*A61K 31/506* (2006.01)

(52) U.S. Cl.
CPC .......... *C07D 403/12* (2013.01); *A61K 31/506* (2013.01)

(58) Field of Classification Search
CPC ............................ A61K 31/506; C07D 403/12
See application file for complete search history.

(56) References Cited

U.S. PATENT DOCUMENTS

| | | | |
|---|---|---|---|
| 2019/0161476 | A1 | 5/2019 | Chen et al. |
| 2021/0078993 | A1 | 3/2021 | Chen et al. |

FOREIGN PATENT DOCUMENTS

| | | | |
|---|---|---|---|
| CN | 109422760 | A | 3/2019 |
| EP | 3459952 | A1 | 3/2019 |
| JP | 2019519512 | A | 7/2019 |
| JP | 2021507927 | A | 2/2021 |
| WO | 2015057938 | A1 | 4/2015 |
| WO | 2015057963 | A1 | 4/2015 |
| WO | 2015059668 | A1 | 4/2015 |
| WO | 2017198221 | A1 | 11/2017 |

OTHER PUBLICATIONS

The Japanese 1st Office Action issued on Oct. 15, 2024 for JP2023-578836.

Noriaki Hirayama, Principles of Crystallization, Handbook of Organic Compound Crystallization, Jul. 2008, pp. 17-23, 37-40, 45-51, 57-65.

Hiroshi Takiyama, Crystallization Operation for Purification of Active Pharmaceutical Ingredients, Japanese Journal of Crystal Growth, vol. 45, No. 4 (2018), Special Feature: Crystal Growth and Medicine, p. 1-8.

The Japanese Decision of Refusal issued on Mar. 11, 2025 for JP2023-578836.

The European search report issued on Jun. 30, 2025 for EP22827556.6.

John F Bauer: "Pharmaceutical Solids—The Amorphous Phase",Journal of Validation Technology,vol. 15, No. 3,Jan. 1, 2009 (Jan. 1, 2009), pp. 63-68, XP055280414,Netherlands Table: Effect of amorphous and crystalline state on physico-chemical properties.

(Continued)

*Primary Examiner* — Jared Barsky
(74) *Attorney, Agent, or Firm* — Yue (Robert) Xu; Apex Attorneys at Law, LLP

(57) ABSTRACT

The present invention relates to the field of chemical pharmacy, relates to a crystal form of a pyrimidine derivative and a preparation method therefor, and specifically relates to crystal forms A, B, C, D, and E of a compound of formula (I), a preparation method therefor, and a pharmaceutical composition and use thereof. The present invention solves the problems of small granularity, poor fluidity, poor stability and the like of the compound of formula (I) present in an amorphous form. The crystal form prepared by the present invention and the pharmaceutical composition thereof can be used for preparing a drug for treating a cancer disease.

Formula I

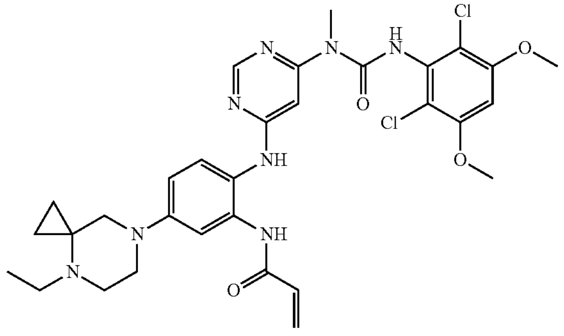

19 Claims, 6 Drawing Sheets

(56) References Cited

OTHER PUBLICATIONS

Mino R Caira Ed—Montchamp Jean-Luc:"Crystalline Polymorphism of Organic Compounds", Topics in Current Chemistry; [Topics in Current Chemistry], Springer, Berlin, DE, vol. 198, Jan. 1, 1998 (Jan. 1, 1998),pp. 163-208,XP001156954,ISSN: 0340-1022, DOI: 10.1007/3-540-69178-2_5.

International Search Report for PCT/CN2022/100065mailed Aug. 18, 2022, ISA/CN.

Alan P. Brown et al., Cartilage Dysplasia and Tissue Mineralization in the Rat Following Administration of a FGF Receptor Tyrosine Kinase Inhibitor, Toxicologic Pathology, 33:449-455, 2005.

Daniela Sia et al., Integrative Molecular Analysis of Intrahepatic Cholangiocarcinoma Reveals 2 Classes That Have Different Outcomes, Gastroenterology 2013.

Dorothy M. French et al., Targeting FGFR4 Inhibits Hepatocellular Carcinoma in Preclinical Mouse Models, PLoS ONE, May 2012 vol. 7, Issue 5 e36713.

CRYSTAL FORM OF PYRIMIDINE DERIVATIVE AND PREPARATION METHOD THEREFOR

FIELD

The present application is the national phase of International Application No. PCT/CN2022/100065, titled "CRYSTAL FORM OF PYRIMIDINE DERIVATIVE AND PREPARATION METHOD THEREFOR", which claims the priority of Chinese Patent Application No. 202110696953.6, filed with the China National Intellectual Property Administration on and titled with "CRYSTAL FORM OF Jun. 23, 2021, PYRIMIDINE DERIVATIVE AND PREPARATION METHOD THEREFOR", the entire disclosures thereof are incorporated herein by reference.

BACKGROUND

The fibroblast growth factor receptor (FGFR) family has four members, FGFR1, FGFR2, FGFR3 and FGFR4, which belong to the receptor tyrosine kinase family of kinases. Binding to FGF results in FGFR dimerization, followed by receptor autophosphorylation and activation of downstream signaling pathways. Receptor activation is sufficient to rejuvenate and activate specific downstream signaling partners involved in regulating diverse processes including cell growth, cell metabolism, and cell survival. Consequently, the FGF/FGFR signaling pathway affects multiple biological processes essential for cell proliferation, migration, infiltration, and angiogenesis of tumors. The four members of the FGFR family differ from each other in their ligand affinity and tissue distribution. The FGFR-4 gene consists of 18 exons in its genomic structure.

The human FGF19 gene is situated at 11q13.1. FGFR4 specifically binds to its ligand FGF19 to inhibit apoptosis and NF-κB signaling, and upregulate the expression of genes related to cell proliferation. Activation of FGFR4 can lead to a decrease in Ikκβ activity in TNF-α-treated cells, accompanied by a reduction in NF-κB distribution in cells and attenuated apoptotic effects. All four FGFR genes are expressed in human liver, but mature liver parenchymal cells (hepatocytes) only express FGFR4 in large amounts. The binding of FGFR4 to its ligand can also regulate the metabolism of bile acids. The balance of cholesterol conversion into bile acids in the body is closely related to various normal physiological functions of the body. Disruption of this balance can cause many diseases in the body, such as fatty liver, arteriosclerosis and other cardiovascular and cerebrovascular diseases. Therefore, the interaction between FGFR4 and FGF19 has emerged as a novel target for development of a cholesterol-lowering drug used for hyperlipidemia.

In recent years, increasing evidence has demonstrated gene amplification mutations in FGFR1, FGFR2, FGFR3, and FGFR4 across various cancers. A large amount of evidence shows the following: what is related to FGFR1 includes gene mutations in breast cancer, non-small cell lung cancer and glioblastoma, fusion protein formation due to gene transposition in acute myeloid leukemia, and overexpression in pancreatic cancer, bladder cancer, prostate cancer and esophageal cancer; what is related to FGFR2 includes gene mutations and amplifications in gastric cancer, breast cancer and uterine cancer, and overexpression in prostate cancer, esophageal cancer, ovarian cancer, pancreatic cancer, brain tumors, and colorectal cancer; what is related to FGFR3 includes gene mutations in multiple myeloma and bladder cancer, and overexpression in ovarian cancer, non-small cell lung cancer, and hepatocellular carcinoma; and what is related to FGFR4 includes gene mutations and overexpression in lung cancer, ovarian cancer, prostate cancer, liver cancer, and cholangiocarcinoma, etc, and overexpression in thyroid cancer, ovarian cancer, etc. (French et al. 2012 PLos ONE7(5): e367313; Sia et al. 2013 Gastrojterology 144: 829-840).

A series of patents of FGFR inhibitors have been disclosed, but there are few patents on selective inhibition of FGFR4. The advantages of FGFR4 selective inhibitors over FGFR inhibitors are less toxicity (Brown, A P et al (2005)), Toxocol. Pathol., 449-455). FGFR4 inhibitors currently in clinical trials include FGF-401 (Novartis, clinical phase II), BLU-554 (Blueprint, clinical phase I) and H3B6527 (Eisai, clinical phase I). Patents of selective inhibition of FGFR4 include WO2015059668, WO2015057938, and WO2015057963, etc. Current research on FGFR4 inhibitors against tumors such as liver cancer is far from sufficient. It is still necessary to research and develop new FGFR4 inhibitors.

WO2017198221A1 discloses a pyrimidine derivative with the structure represented by the following formula I, whose molecular formula is $C_{31}H_{36}Cl_2N_8O_4$ and whose chemical name is N-(2-((6-(3-(2,6-dichloro-3,5-dimethoxyphenyl)-1-methylureido)pyrimidin-4-yl)amino)-5-(4-eth yl-4,7-diazaspiro[2.5]octan-7-yl)phenyl)acrylamide.

Formula I

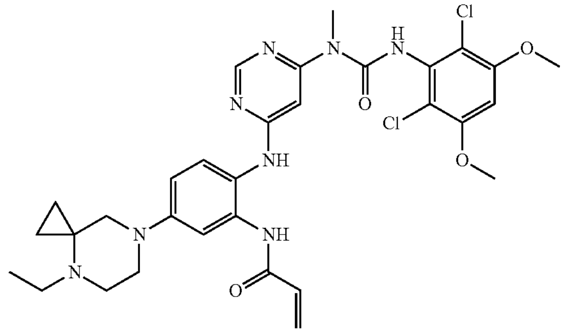

However, for the compound of formula I disclosed in WO2017198221A1, the white solid prepared by the preparation method thereof is in an amorphous form, and its stability, granularity, fluidity, hygroscopicity, etc. are still not satisfactory. In particular, it has small granularity and poor fluidity, which is not suitable for the forming process of solid preparations (such as tablets, capsules or granules). In addition, good stability will bring great benefits for the later use of the compound of Formula I. For example, in the production of solid preparations, the properties of raw materials need to be stable, and active pharmaceutical ingredient and preparations need to maintain stable product quality over a long shelf life.

The preparation of dosage forms facilitates the accurate delivery of precise doses of drugs. However, it is known that the preparation of dosage forms depends on factors such as, but not limited to, solubility, homogeneity, hygroscopicity and fluidity of the drug. Therefore, there is a need for crystal forms of the compound of formula I having excellent properties.

Currently, in the prior art, there is neither a form of the compound of formula I with satisfactory stability, nor report on the crystal form of the compound of formula I. The inventors have obtained the crystal forms of the compound of formula I through a large number of experiments.

SUMMARY

Therefore, in view of the above-mentioned problems in the prior art, the present disclosure provides crystal forms of the compound of formula I N-(2-((6-(3-(2,6-dichloro-3,5-dimethoxyphenyl)-1-methylureido)pyrimidin-4-yl)amino)-5-(4-eth yl-4,7-diazaspiro[2.5]octan-7-yl)phenyl)acrylamide with the following structure, and preparation methods thereof.

Formula I

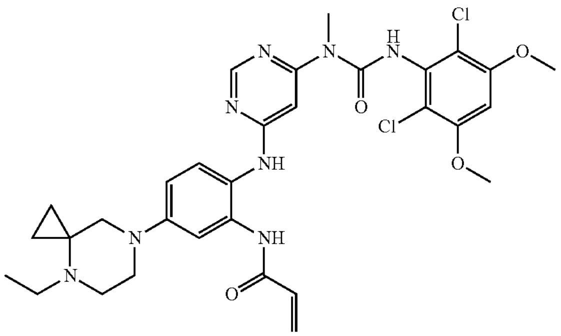

In a first aspect, the present disclosure provides a crystal form A of the compound of formula I (hereinafter referred to as "crystal form A").

For the crystal form A, its X-ray powder diffraction (XRPD) pattern with Cu-Kα radiation shows characteristic peaks at 2θ of 7.3±0.2°, 8.4±0.2°, 9.7±0.2°, 12.4±0.2°, 16.7±0.2°, and 19.5±0.2° in degrees.

Preferably, for the crystal form A, its X-ray powder diffraction pattern with Cu-Kα radiation shows characteristic peaks at 2θ of 7.3±0.2°, 8.4±0.2°, 9.7±0.2°, 12.4±0.2°, 16.7±0.2°, 19.5±0.2°, 21.7±0.2°, 23.5±0.2°, and 28.6±0.2° in degrees.

More preferably, for the crystal form A, its X-ray powder diffraction pattern with Cu-Kα radiation shows characteristic peaks and relative intensities at 2θ of the following positions in degrees:

TABLE 1

| Peak number | 2θ (°) | d (Å) | Relative intensity (%) |
|---|---|---|---|
| 1 | 5.3 | 16.5 | 3.7 |
| 2 | 7.3 | 12.2 | 16.6 |
| 3 | 8.4 | 10.6 | 37.5 |
| 4 | 9.7 | 9.1 | 43.6 |
| 5 | 12.0 | 7.4 | 6.1 |
| 6 | 12.4 | 7.1 | 34.3 |
| 7 | 15.1 | 5.9 | 11.1 |
| 8 | 15.4 | 5.7 | 6.9 |
| 9 | 16.3 | 5.4 | 20.4 |
| 10 | 16.7 | 5.3 | 82.3 |
| 11 | 17.1 | 5.2 | 29.5 |
| 12 | 17.9 | 5.0 | 24.2 |
| 13 | 18.9 | 4.7 | 21.2 |
| 14 | 19.5 | 4.6 | 100 |
| 15 | 21.1 | 4.2 | 14.4 |
| 16 | 21.7 | 4.1 | 31.6 |
| 17 | 22.7 | 3.9 | 3.7 |
| 18 | 23.1 | 3.9 | 9.1 |
| 19 | 23.5 | 3.8 | 20.4 |
| 20 | 24.8 | 3.6 | 14.4 |
| 21 | 25.4 | 3.5 | 14.6 |
| 22 | 25.8 | 3.4 | 12.3 |
| 23 | 26.3 | 3.4 | 8.6 |
| 24 | 27.1 | 3.3 | 8.2 |
| 25 | 27.7 | 3.2 | 7.3 |
| 26 | 28.2 | 3.2 | 2.8 |
| 27 | 28.6 | 3.1 | 31.3 |
| 28 | 29.0 | 3.1 | 23.5 |
| 29 | 30.9 | 2.9 | 3.1 |
| 30 | 31.5 | 2.8 | 2 |
| 31 | 32.7 | 2.7 | 5.5 |
| 32 | 34.1 | 2.6 | 5 |
| 33 | 35.9 | 2.5 | 5.4 |
| 34 | 38.1 | 2.4 | 3.7 |

More preferably, the X-ray powder diffraction pattern of the crystal form A is substantially as shown in FIG. 1.

Further, the differential scanning calorimetry (DSC) curve of the crystal form A has an endothermic peak at 208-212° C., and the DSC curve is substantially as shown in FIG. 2.

Correspondingly, the present disclosure provides a method for preparing the crystal form A, which is any one selected from the group consisting of:

- method (1), comprising steps of mixing the compound of formula I with an organic solvent to obtain a suspension, stirring the suspension at 5-50° C. for 1-7 days, separating solid, and drying the solid under vacuum at 20-60° C. for 8-24 h to obtain the crystal form A, wherein the organic solvent is which is any one selected from the group consisting of $C_1$-$C_3$ alcohol, methyl acetate, ethyl acetate, acetone, acetonitrile, and a mixture thereof;
- preferably, the $C_1$-$C_3$ alcohol in method (1) is which is any one selected from the group consisting of methanol, ethanol, n-propanol and isopropanol;
- preferably, a weight-volume ratio of the compound of formula I to the organic solvent in method (1) is 1:2-1:50 (g/mL);
- method (2), comprising steps of mixing the compound of formula I with DMSO or dichloromethane, stirring at 20-50° C. to obtain a clear solution after dissolution, adding a poor solvent, stirring until precipitation, separating solid, and drying the solid under vacuum at 20-60° C. for 8-24 h to obtain the crystal form A, wherein the poor solvent is which is any one selected from the group consisting of $C_1$-$C_4$ alcohol, methyl acetate, ethyl acetate, butyl acetate, isopropyl acetate, acetone, acetonitrile, water, an alkane, and a mixture thereof;
- preferably, the $C_1$-$C_4$ alcohol in method (2) is which is any one selected from the group consisting of methanol, ethanol and isopropanol, and the alkane is which is any one selected from the group consisting of n-heptane, n-hexane and cyclohexane;
- preferably, a weight-volume ratio of the compound of formula I to DMSO or dichloromethane in method (2) is 1:10-1:40 (g/mL);
- preferably, a weight-volume ratio of the compound of formula I to the poor solvent in method (2) is 1:20-1:130 (g/mL);
- method (3), comprising steps of mixing the compound of formula I with DMF, stirring at 20-50° C. to obtain a clear solution after dissolution, adding a poor solvent, stirring until precipitation, separating solid, and drying the solid under vacuum at 20-60° C. for 8-24 h to obtain the crystal form A;

preferably, the poor solvent in method (3) is which is any one selected from the group consisting of $C_2$-$C_4$ alcohol, isopropyl acetate, acetone, acetonitrile, water, and a mixture thereof;

preferably, the $C_2$-$C_4$ alcohol in method (3) is ethanol or isopropanol;

preferably, a weight-volume ratio of the compound of formula I to DMF in method (3) is 1:5-1:20 (g/mL);

preferably, a weight-volume ratio of the compound of formula I to the poor solvent in method (3) is 1:20-1:100 (g/mL);

method (4), comprising steps of mixing the compound of formula I with DMAC, stirring at 20-50° C. to obtain a clear solution after dissolution, adding a poor solvent, stirring until precipitation, separating solid, and drying the solid under vacuum at 20-60° C. for 8-24 h to obtain the crystal form A, wherein a weight-volume ratio of the compound of formula I to DMAC is 1:6-1:30 (g/mL);

preferably, the poor solvent in method (4) is which is any one selected from the group consisting of $C_1$-$C_4$ alcohol, water, and a mixture thereof;

preferably, the $C_1$-$C_4$ alcohol in method (4) is which is any one selected from the group consisting of methanol, ethanol and isopropanol;

preferably, a weight-volume ratio of the compound of formula I to the poor solvent in method (4) is 1:20-1:100 (g/mL); and method (5), comprising steps of mixing the compound of formula I with n-butanol to obtain a suspension, stirring the suspension at 5-40° C. for 1-7 days, separating solid, and drying the solid under vacuum at 20-60° C. for 8-24 h to obtain the crystal form A;

preferably, a weight-volume ratio of the compound of formula I to n-butanol in method (5) is 1:2-1:50 (g/mL).

In another aspect, the present disclosure provides a crystal form B of the compound of formula I (hereinafter referred to as "crystal form B").

For the crystal form B, its X-ray powder diffraction (XRPD) pattern with Cu-Kα radiation shows characteristic peaks at 2θ of 7.9±0.2°, 9.4±0.2°, 10.1±0.2°, 11.9±0.2°, 14.4±0.2°, 16.1±0.2° and 19.0±0.2° in degrees.

Preferably, for the crystal form B, its X-ray powder diffraction pattern with Cu-Kα radiation shows characteristic peaks at 2θ of 7.9±0.2°, 9.4±0.2°, 10.1±0.2°, 11.9±0.2°, 14.4±0.2°, 16.1±0.2°, 16.9±0.2°, 19.0±0.2°, 19.3±0.2°, 21.7±0.2°, and 22.4±0.2° in degrees.

More preferably, for the crystal form B, its X-ray powder diffraction pattern with Cu-Kα radiation shows characteristic peaks and relative intensities at 2θ of the following positions in degrees:

TABLE 2

| Peak number | 2θ (°) | d (Å) | Relative intensity (%) |
|---|---|---|---|
| 1 | 7.9 | 11.2 | 39.2 |
| 2 | 9.4 | 9.4 | 53.2 |
| 3 | 10.1 | 8.8 | 74.9 |
| 4 | 11.9 | 7.4 | 87.9 |
| 5 | 12.5 | 7.1 | 18.9 |
| 6 | 12.8 | 6.9 | 34.1 |
| 7 | 13.5 | 6.6 | 13.3 |
| 8 | 14.4 | 6.1 | 77 |
| 9 | 14.8 | 6.0 | 16.8 |
| 10 | 15.2 | 5.8 | 3.6 |
| 11 | 16.1 | 5.5 | 59.2 |
| 12 | 16.9 | 5.2 | 51.2 |
| 13 | 18.4 | 4.8 | 17.8 |
| 14 | 19.0 | 4.7 | 100 |
| 15 | 19.3 | 4.6 | 60.5 |
| 16 | 19.7 | 4.5 | 25.8 |
| 17 | 20.3 | 4.4 | 7.1 |
| 18 | 20.7 | 4.3 | 4.7 |
| 19 | 21.4 | 4.1 | 28.3 |
| 20 | 21.7 | 4.1 | 59.9 |
| 21 | 22.4 | 4.0 | 68.4 |
| 22 | 23.3 | 3.8 | 35.3 |
| 23 | 24.0 | 3.7 | 60.4 |
| 24 | 24.5 | 3.6 | 10 |
| 25 | 25.0 | 3.6 | 21.4 |
| 26 | 25.4 | 3.5 | 16.2 |
| 27 | 25.9 | 3.4 | 50.5 |
| 28 | 26.4 | 3.4 | 44.7 |
| 29 | 27.6 | 3.2 | 8.3 |
| 30 | 28.5 | 3.1 | 20.7 |
| 31 | 31.2 | 2.9 | 11.1 |
| 32 | 33.2 | 2.7 | 15.4 |

More preferably, the X-ray powder diffraction pattern of the crystal form B is substantially as shown in FIG. 3.

Further, the differential scanning calorimetry (DSC) curve of the crystal form B has an endothermic peak at 195-201° C., and the DSC curve is substantially as shown in FIG. 4.

Correspondingly, the present disclosure provides a method for preparing the crystal form B, which is any one selected from the group consisting of:

method (1), comprising steps of mixing the compound of formula I with dichloromethane, stirring at 20-30° C. to obtain a clear solution after dissolution, adding a poor solvent, stirring until precipitation, separating solid, and drying the solid under vacuum at 20-60° C. for 8-24 h to obtain the crystal form B, wherein the poor solvent is a mixture of isobutyl acetate and n-heptane;

preferably, a weight-volume ratio of the compound of formula I to dichloromethane in method (1) is 1:10-1:30 (g/mL);

preferably, a weight-volume ratio of the compound of formula I to the poor solvent in method (1) is 1:20-1:100 (g/mL); and method (2), comprising steps of mixing the compound of formula I with a solvent to obtain a suspension, stirring the suspension at 5-50° C. for 1-7 days, separating solid, and drying the solid under vacuum at 20-60° C. for 8-24 h to obtain the crystal form B, wherein the solvent is which is any one selected from the group consisting of 2-butanone, methyl isobutyl ketone, 1,4-dioxane, butyl acetate, isopropyl acetate, isobutyl acetate, n-heptane, n-hexane, cyclohexane, water, and a mixture thereof;

preferably, a weight-volume ratio of the compound of formula I to the solvent in method (2) is 1:2-1:50 (g/mL).

In another aspect, the present disclosure provides a crystal form C of the compound of formula I (hereinafter referred to as "crystal form C").

For the crystal form C, its X-ray powder diffraction (XRPD) pattern with Cu-Kα radiation shows characteristic peaks at 2θ of 7.3±0.2°, 12.4±0.2°, 12.8±0.2°, 14.8-0.2°, 18.4=0.2°, 19.5±0.2° and 23.0±0.2° in degrees.

Preferably, for the crystal form C, its X-ray powder diffraction pattern with Cu-Kα radiation shows characteristic peaks at 2θ of 7.3±0.2°, 12.4±0.2°, 12.8±0.2°, 14.8=0.2°, 18.4=0.2°, 19.5±0.2°, 20.8±0.2°, 23.0±0.2°, 23.3±0.2°, 24.3±0.2°, and 26.0±0.2° in degrees.

More preferably, for the crystal form C, its X-ray powder diffraction pattern with Cu-Kα radiation shows characteristic peaks and relative intensities at 2θ of the following positions in degrees:

TABLE 3

| Peak number | 2θ (°) | d (Å) | Relative intensity (%) |
|---|---|---|---|
| 1 | 3.6 | 24.5 | 9.1 |
| 2 | 7.3 | 12.1 | 20.1 |
| 3 | 10.6 | 8.3 | 2.6 |
| 4 | 11.0 | 8.1 | 21.8 |
| 5 | 11.3 | 7.8 | 26.9 |
| 6 | 11.8 | 7.5 | 8 |
| 7 | 12.4 | 7.2 | 80.7 |
| 8 | 12.8 | 6.9 | 35.1 |
| 9 | 13.6 | 6.5 | 12 |
| 10 | 14.3 | 6.2 | 11.6 |
| 11 | 14.8 | 6.0 | 47.3 |
| 12 | 16.8 | 5.3 | 14.2 |
| 13 | 17.7 | 5.0 | 35.6 |
| 14 | 18.0 | 4.9 | 29.1 |
| 15 | 18.4 | 4.8 | 100 |
| 16 | 19.5 | 4.5 | 70.1 |
| 17 | 20.3 | 4.4 | 21.2 |
| 18 | 20.8 | 4.3 | 52.4 |
| 19 | 21.4 | 4.2 | 9.1 |
| 20 | 22.0 | 4.0 | 34.2 |
| 21 | 23.0 | 3.9 | 65.6 |
| 22 | 23.3 | 3.8 | 44 |
| 23 | 23.9 | 3.7 | 25 |
| 24 | 24.3 | 3.7 | 32.8 |
| 25 | 24.7 | 3.6 | 20.8 |
| 26 | 26.0 | 3.4 | 55.9 |
| 27 | 26.9 | 3.3 | 10.9 |
| 28 | 27.5 | 3.2 | 11.2 |
| 29 | 28.2 | 3.2 | 14.7 |
| 30 | 29.0 | 3.1 | 6.7 |
| 31 | 30.0 | 3.0 | 18.7 |
| 32 | 31.4 | 2.8 | 14.2 |

More preferably, the X-ray powder diffraction pattern of the crystal form C is substantially as shown in FIG. 5.

Further, the differential scanning calorimetry (DSC) curve of the crystal form C has an endothermic peak at 161-168° C., and the DSC curve is substantially as shown in FIG. 6.

Correspondingly, the present disclosure provides a method for preparing the crystal form C, which is any one selected from the group consisting of:

method (1), comprising steps of mixing the compound of formula I with DMAC to obtain a suspension, stirring the suspension at 50-70° C. for 8-24 h, separating solid, and drying the solid under vacuum at 20-60° C. for 8-24 h to obtain the crystal form C, wherein a weight-volume ratio of the compound of formula I to DMAC is 1:2-1:5 (g/mL); and method (2), comprising steps of mixing the compound of formula I with DMAC, stirring at 55-70° C. to obtain a clear solution after dissolution, adding a poor solvent, stirring until precipitation, separating solid, and drying the solid under vacuum at 20-60° C. for 8-24 h to obtain the crystal form C, wherein a weight-volume ratio of the compound of formula I to DMAC is 1:6-1:30 (g/mL);

preferably, the poor solvent in method (2) is which is any one selected from the group consisting of n-propanol, isopropanol, n-butanol, $C_3$-$C_6$ ester and acetone;

preferably, the $C_3$-$C_6$ ester in method (2) is which is any one selected from the group consisting of methyl acetate, ethyl acetate, isopropyl acetate and isobutyl acetate;

preferably, a weight-volume ratio of the compound of formula I to the poor solvent in method (2) is 1:10-1:50 (g/mL).

In another aspect, the present disclosure provides a crystal form D of the compound of formula I (hereinafter referred to as "crystal form D").

For the crystal form D, its X-ray powder diffraction (XRPD) pattern with Cu-Kα radiation shows characteristic peaks at 2θ of 3.5±0.2°, 7.0±0.2°, 13.4=0.2°, 15.7=0.2°, 16.6±0.2°, and 20.6±0.2° in degrees.

Preferably, for the crystal form D, its X-ray powder diffraction pattern with Cu-Kα radiation shows characteristic peaks at 2θ of 3.5±0.2°, 7.0±0.2°, 12.0±0.2°, 13.4±0.2°, 15.7±0.2°, 16.6=0.2°, 20.1±0.2°, 20.6±0.2°, 22.1±0.2°, and 24.9±0.2° in degrees.

More preferably, for the crystal form D, its X-ray powder diffraction pattern with Cu-Kα radiation shows characteristic peaks and relative intensities at 2θ of the following positions in degrees:

TABLE 4

| Peak number | 2θ (°) | d (Å) | Relative intensity (%) |
|---|---|---|---|
| 1 | 3.5 | 25.2 | 35.9 |
| 2 | 7.0 | 12.6 | 25.7 |
| 3 | 10.5 | 8.4 | 5.6 |
| 4 | 11.0 | 8.1 | 24.3 |
| 5 | 11.5 | 7.7 | 12.7 |
| 6 | 12.0 | 7.4 | 46.2 |
| 7 | 12.4 | 7.2 | 18.3 |
| 8 | 13.4 | 6.6 | 100 |
| 9 | 14.0 | 6.3 | 13.4 |
| 10 | 14.4 | 6.1 | 9.9 |
| 11 | 15.7 | 5.6 | 53.5 |
| 12 | 16.6 | 5.3 | 17.2 |
| 13 | 17.7 | 5.0 | 30.6 |
| 14 | 18.3 | 4.8 | 22.2 |
| 15 | 18.6 | 4.8 | 45.3 |
| 16 | 20.1 | 4.4 | 72.3 |
| 17 | 20.6 | 4.3 | 85 |
| 18 | 21.2 | 4.2 | 9.5 |
| 19 | 21.7 | 4.1 | 42.2 |
| 20 | 22.1 | 4.0 | 69.7 |
| 21 | 22.4 | 4.0 | 23.4 |
| 22 | 23.3 | 3.8 | 33.8 |
| 23 | 24.3 | 3.7 | 12.3 |
| 24 | 24.9 | 3.6 | 70.7 |
| 25 | 25.9 | 3.4 | 9.9 |
| 26 | 27.0 | 3.3 | 23.2 |
| 27 | 27.3 | 3.3 | 28 |
| 28 | 28.4 | 3.1 | 9.4 |
| 29 | 29.0 | 3.1 | 10.2 |
| 30 | 29.3 | 3.0 | 11.6 |
| 31 | 30.1 | 3.0 | 11.3 |
| 32 | 31.7 | 2.8 | 20.3 |

More preferably, the X-ray powder diffraction pattern of the crystal form D is substantially as shown in FIG. 7.

Further, the differential scanning calorimetry (DSC) curve of the crystal form D has an endothermic peak at 150-158° C., and the DSC curve is substantially as shown in FIG. 8.

Correspondingly, the present disclosure provides a method for preparing the crystal form D, comprising mixing the compound of formula I with DMF, stirring at 50-70° C. to obtain a clear solution after dissolution, adding methanol, cooling down to 20-30° C., stirring until precipitation, separating solid, and drying the solid under vacuum at 20-60° C. for 8-24 h to obtain the crystal form D;

preferably, a weight-volume ratio of the compound of formula I to DMF is 1:10-1:30 (g/mL);

preferably, a weight-volume ratio of the compound of formula I to methanol is 1:20-1:50 (g/mL).

In another aspect, the present disclosure provides a crystal form E of the compound of formula I (hereinafter referred to as "crystal form E").

For the crystal form E, its X-ray powder diffraction (XRPD) pattern with Cu-Kα radiation shows characteristic peaks at 2θ of 3.5±0.2°, 7.0±0.2°, 13.5±0.2°, 15.2±0.2°, 16.3=0.2°, 17.5±0.2° and 28.7±0.2° in degrees.

Preferably, for the crystal form E, its X-ray powder diffraction pattern with Cu-Kα radiation shows characteristic peaks at 2θ of 3.5±0.2°, 7.0±0.2°, 13.5±0.2°, 15.2±0.2°, 16.3±0.2°, 17.5±0.2°, 18.8±0.2°, 20.2±0.2°, 22.1±0.2°, 25.0±0.2°, and 28.7±0.2° in degrees.

More preferably, for the crystal form E, its X-ray powder diffraction pattern with Cu-Kα radiation shows characteristic peaks and relative intensities at 2θ of the following positions in degrees:

TABLE 5

| Peak number | 2θ (°) | d (Å) | Relative intensity (%) |
|---|---|---|---|
| 1 | 3.5 | 25.4 | 58.1 |
| 2 | 7.0 | 12.7 | 38.1 |
| 3 | 10.5 | 8.4 | 8.5 |
| 4 | 11.0 | 8.0 | 33.2 |
| 5 | 11.6 | 7.6 | 19.7 |
| 6 | 11.9 | 7.4 | 38.2 |
| 7 | 12.4 | 7.1 | 21.6 |
| 8 | 13.5 | 6.6 | 94.6 |
| 9 | 13.7 | 6.4 | 29.9 |
| 10 | 14.4 | 6.1 | 12 |
| 11 | 15.2 | 5.8 | 96.5 |
| 12 | 16.3 | 5.4 | 26.8 |
| 13 | 16.9 | 5.2 | 10.6 |
| 14 | 17.5 | 5.1 | 70.8 |
| 15 | 18.2 | 4.9 | 18.4 |
| 16 | 18.8 | 4.7 | 73.6 |
| 17 | 19.6 | 4.5 | 33.2 |
| 18 | 20.2 | 4.4 | 88.4 |
| 19 | 20.8 | 4.3 | 21.2 |
| 20 | 21.3 | 4.2 | 35.1 |
| 21 | 21.8 | 4.1 | 31.2 |
| 22 | 22.1 | 4.0 | 75 |
| 23 | 22.8 | 3.9 | 42.5 |
| 24 | 23.2 | 3.8 | 7.2 |
| 25 | 23.6 | 3.8 | 16.8 |
| 26 | 25.0 | 3.6 | 100 |
| 27 | 25.4 | 3.5 | 8.7 |
| 28 | 26.5 | 3.4 | 6 |
| 29 | 27.3 | 3.3 | 39.8 |
| 30 | 27.7 | 3.2 | 19 |
| 31 | 28.7 | 3.1 | 19.2 |
| 32 | 29.3 | 3.0 | 13.7 |
| 33 | 30.2 | 3.0 | 12.1 |
| 34 | 31.3 | 2.9 | 21.9 |

More preferably, the X-ray powder diffraction pattern of the crystal form E is substantially as shown in FIG. 9.

Further, the differential scanning calorimetry (DSC) curve of the crystal form E has an endothermic peak at 131-145° C., and the DSC curve is substantially as shown in FIG. 10.

Correspondingly, the present disclosure provides a method for preparing the crystal form E, which is any one selected from the group consisting of:

method (1), comprising steps of mixing the compound of formula I with DMF, stirring at 20-30° C. to obtain a clear solution after dissolution, adding to a poor solvent, stirring until precipitation, separating solid, and drying the solid under vacuum at 20-60° C. for 8-24 h to obtain the crystal form E;

preferably, the poor solvent in method (1) is a mixed solvent selected from the group consisting of ethanol, acetone, acetonitrile and water;

preferably, a weight-volume ratio of the compound of formula I to DMF in method (1) is 1:5-1:20 (g/mL);

preferably, a weight-volume ratio of the compound of formula I to the poor solvent in method (1) is 1:20-1:100 (g/mL); and method (2), comprising steps of mixing the compound of formula I with DMAC, stirring at 20-30° C. to obtain a clear solution after dissolution, adding to a poor solvent, stirring until precipitation, separating solid, and drying the solid under vacuum at 20-60° C. for 8-24 h to obtain the crystal form E, wherein a weight-volume ratio of the compound of formula I to DMAC is 1:6-1:30 (g/mL);

preferably, the poor solvent in method (2) is a mixed solvent selected from the group consisting of ethanol, n-propanol and water;

preferably, a weight-volume ratio of the compound of formula I to the poor solvent in method (2) is 1:70-1:100 (g/mL).

In another aspect, the present disclosure provides a pharmaceutical composition comprising a therapeutically effective amount of the crystal form A, the crystal form B, the crystal form C, the crystal form D, or the crystal form E as an active ingredient. Preferably, in the pharmaceutical composition, the crystal form A, the crystal form B, the crystal form C, the crystal form D, or the crystal form E can be mixed with one or more pharmaceutically acceptable solid or liquid diluents and/or excipients to prepare into a galenic preparation.

In yet another aspect, the present disclosure provides use of the crystal form A, the crystal form B, the crystal form C, the crystal form D, or the crystal form E, or a pharmaceutical composition thereof in the manufacture of a medicament for treating a disease of cancer, wherein the disease is which is any one selected from the group consisting of non-small cell lung cancer, gastric cancer, multiple myeloma, liver cancer, and cholangiocarcinoma, preferably liver cancer or cholangiocarcinoma.

DETAILED DESCRIPTION

Figure 1:
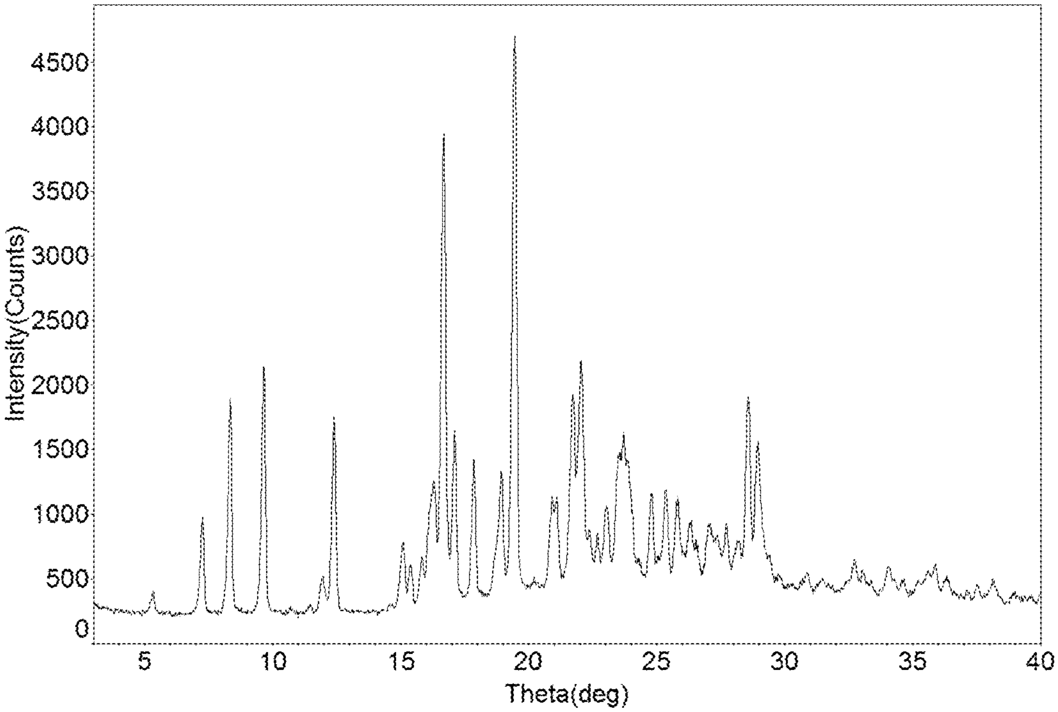
FIG. 1 is the X-ray powder diffraction pattern of the crystal form A prepared in Example 1.

The present disclosure will be described in further detail below. It should be understood that the expressions are intended to describe, but not to limit the present disclosure.

General Definitions and Terms

Unless otherwise specified, the technical and scientific terms used herein have the same meanings as commonly understood by those skilled in the art to which the present disclosure belongs. In case of conflict, the definition provided in this application will prevail. When expressing a certain amount, concentration, or other value or parameter in the form of a range, a preferred range, or a preferred upper limit and a preferred lower limit, it should be understood that it is equivalent to specifically disclosing any range by combining any pair of upper limit of the range or preferred value with any lower limit of the range or preferred value, regardless of whether the range is specifically disclosed. Unless otherwise specified, the numerical ranges listed herein are intended to include the endpoints of the range and all integers and fractions (decimals) within the range.

The terms "about" and "approximately" when used with a numerical variable usually mean that the numerical value of the variable and all the numerical values of the variable are within experimental error (for example, within the 95% confidence interval of the mean) or within +10% of the specified value, or within a wider range.

The expression "comprise" or the synonymous similar expressions "include", "contain" and "have" are open-ended, and do not exclude additional unlisted elements, steps or components. The expression "consist of" excludes any unspecified elements, steps or components. The expression "essentially consist of" means that the scope is limited to the specified elements, steps or components, plus optional and new elements, steps or components that do not substantially affect the claimed subject matter. It should be understood that the expression "comprise"/"comprising" encompasses the expressions "essentially consist of" and "consist of".

The term "optional" or "optionally" as used herein means that the event or situation subsequently described may or may not occur, and the expression includes the occurrence of the event or situation and the non-occurrence of the event or situation.

Unless otherwise specified, the percentages, parts, and the like used herein are all by weight.

As used herein, the term "crystal form" or "crystal" refers to any solid substance exhibiting a three-dimensional order, and producing a characteristic X-ray powder diffraction pattern with clearly-defined peaks, contrary to amorphous solid substances.

As used herein, the term "X-ray powder diffraction (XRPD) pattern" refers to an experimentally observed diffraction pattern or a parameter, data or value derived therefrom. The XRPD pattern is usually characterized by peak position (abscissa) and/or peak intensity (ordinate).

As used herein, the term "2θ" refers to the peak position expressed in degrees)(°) based on the setting in the X-ray diffraction experiment, and is usually the unit of abscissa in the diffraction pattern. If when the incident beam forms an angle θ with a certain lattice plane, the reflection is diffracted, the experimental setup needs to record the reflected beam at an angle of 2θ. It should be understood that the specific 20 value of the specific crystal form mentioned herein is intended to mean the 20 value (in degrees) measured using the X-ray diffraction experimental conditions described herein. For example, as described herein, Cu-Kα (Kα1 is 1.5418 Å) is used as the radiation source. The XRPD pattern herein can be collected, for example, on Rigaku MiniFlex-600 X-ray powder diffraction analyzer. Exemplary test conditions may be a scanning speed of 10°/min and a scanning step width of 0.01°.

As used herein, the term "substantially" for X-ray diffraction peaks means to take into account variations in the position and intensity of the representative peaks. For example, those skilled in the art will understand that the peak position (2θ) will show some changes, usually as much as 0.1-0.2 degrees (±0.1 to ±0.2 degrees), and the instrument used to measure diffraction will also cause some changes. In addition, those skilled in the art will understand that the relative peak intensity will vary due to differences between instruments, and the degree of crystallinity, preferred orientation, prepared sample surface, and other factors known to those skilled in the art, and should be regarded as merely a qualitative measurement.

As used herein, differential scanning calorimetry (DSC) measures the transition temperature when a crystal absorbs or releases heat due to a change in its crystal structure or melting of the crystal. For the same crystal form of the same compound, in continuous analysis, the error of thermal transition temperature and melting point is typically within about 5° C. When a compound is described as having a given DSC peak or melting point, it means that the DSC peak or melting point is +5° C. "Substantially" also takes these temperature change into account. DSC provides an auxiliary method to distinguish different crystal forms. Different crystal forms can be identified according to their different transition temperature characteristics. It should be pointed out that for a mixture, its DSC peak or melting point may vary in a larger range. In addition, due to the decomposition of the substance in the process of melting, the melting temperature is related to the heating rate. DSC curve can be measured, for example, on an instrument such as model NETZSCH DSC214. Exemplary test conditions include heating rate of 10° C./min and temperature range of 25-250° C.

Beneficial Effect

The crystal forms of the compound of formula I of the present disclosure have simple crystallization process and convenient operation, and can realize industrial-scale production. Moreover, the crystal forms of the present disclosure have the advantages of high product purity, excellent physical and chemical properties, good chemical and physical stability to high temperature/high humidity, excellent processing (filtration, drying, dissolution and tableting) adaptability, reproducibility, low hygroscopicity, and good fluidity, which are more conducive to the processing and the improvement of finished drug properties. In addition, they have good solubility, dissolution, dissolution time and biological release, which have a good market application prospect.

DETAILED DESCRIPTION

The present disclosure will be further illustrated by way of the following examples, which are only described to better understand the content of the present disclosure, and do not constitute a restriction or limitation to the protection scope of the present disclosure.

Preparation and Characterization of the Crystal Form of the Compound of Formula I

Preparation Example

Figure 11:
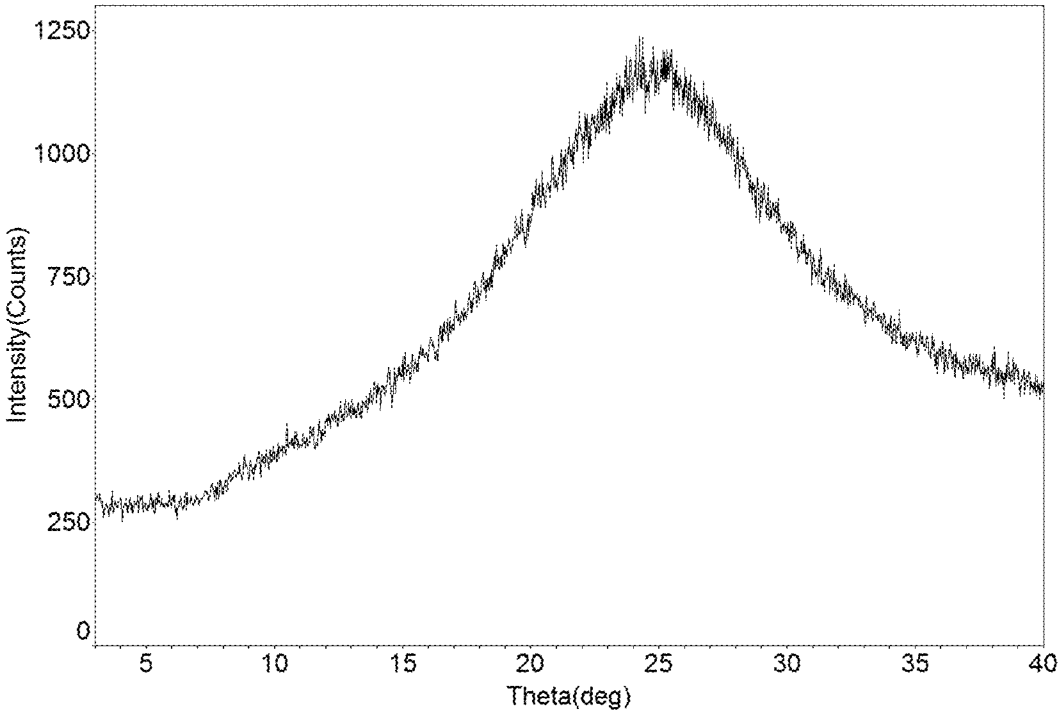
FIG. 11 is the X-ray powder diffraction pattern of the white amorphous solid obtained in Preparation Example.

The compound of formula I described in the examples of the present disclosure was prepared according to the method in Example 5 of WO2017198221A1. Specifically, tert-butyl-N-[6-[tert-butoxycarbonyl(2,6-dichloro-3,5-dimethoxyphenyl)carbamoyl]methylamin o]pyrimidin-4-yl]-N-[4-(8- ethyl-5,8-diazaspiro[2.5]octan-5-yl)-2(prop-2-enoylamino) phenyl]carb amic acid 5i (440 mg, 0.514 mmol) was dissolved in 15 mL of dichloromethane, added with 5 mL of trifluoroacetic acid, and reacted at room temperature for 12 h. The reaction solution was then concentrated under reduced pressure, added with 20 mL of ethyl acetate, washed with saturated sodium carbonate solution (20 mL) followed by saturated sodium chloride solution (20 mL), dried over anhydrous sodium sulfate, filtered, and concentrated under reduced pressure. The obtained residue was purified by silica gel thin layer chromatography (eluent: B system) to obtain N-(2-((6-(3-(2,6-dichloro-3,5-dimethoxyphenyl)-1-methylureido)pyrimidin-4-yl)amino)-5-(4-eth yl-4,7-diazaspiro [2.5]octan-7-yl)phenyl)acrylamide 5 (100 mg, white solid). The obtained white solid was amorphous as determined by XRPD, and its X-ray powder diffraction pattern is shown in FIG. 11.

Information of Test Instrument and Test Methods

X-ray powder diffraction instrument and test conditions involved in the present disclosure: the model of the X-ray diffraction instrument was Rigaku MiniFlex-600 Cu target; the operation method included a scanning speed of 10°/min and scanning step width of 0.01°.

DSC test conditions involved in the present disclosure: the model of the DSC detector was NETZSCH DSC214; the operation method included a heating rate of 10° C./min and temperature range of 25-250° C.

High-performance liquid chromatography (HPLC) test conditions involved in the present disclosure: the model of the liquid chromatograph was Agilent 1260; the chromatographic column was Waters XBridge C18 150*4.6 mm 3.5 μm; the detection wavelength was 234 nm; and the column temperature was 25° C.

Figure 2:
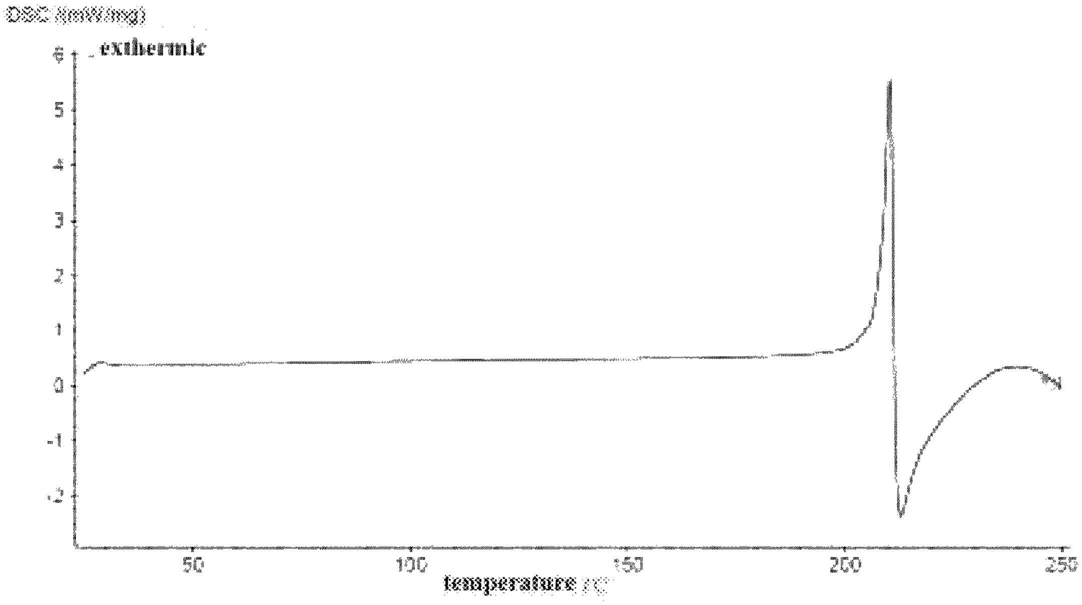
FIG. 2 is the DSC curve of the crystal form A prepared in Example 1.

Example 1 Preparation of Crystal Form A 0.1 g of the compound of formula I was mixed with 0.2 mL of methanol to obtain a suspension, which was then stirred at 5° C. for one day, and the solid was separated. The filter cake was then dried under vacuum at 50° C. for 24 h to obtain 0.082 g of solid as crystal form A. Its X-ray powder diffraction pattern and DSC curve are shown in FIGS. 1-2, respectively.

Example 2 Preparation of Crystal Form A 0.1 g of the compound of formula I was mixed with 5 mL of ethanol to obtain a suspension, which was then stirred at 50° C. for three days, and the solid was separated. The filter cake was then dried under vacuum at 50° C. for 24 h to obtain 0.078 g of solid as crystal form A. The X-ray powder diffraction pattern and DSC curve are consistent with FIGS. 1-2, respectively.

Example 3 Preparation of Crystal Form A 0.1 g of the compound of formula I was mixed with 1 mL of isopropanol to obtain a suspension, which was then stirred at 25° C. for one day, and the solid was separated. The filter cake was then dried under vacuum at 50° C. for 24 h to obtain 0.075 g of solid as crystal form A. Its X-ray powder diffraction pattern and DSC curve are consistent with FIGS. 1-2, respectively.

Example 4 Preparation of Crystal Form A 0.1 g of the compound of formula I was mixed with 2 mL of n-butanol to obtain a suspension, which was then stirred at 25° C. for five days, and the solid was separated. The filter cake was then dried under vacuum at 40° C. for 24 h to obtain 0.072 g of solid as crystal form A. Its X-ray powder diffraction pattern and DSC curve are consistent with FIGS. 1-2, respectively.

Example 5 Preparation of Crystal Form A 0.1 g of the compound of formula I was mixed with 0.5 mL of methyl acetate to obtain a suspension and stirred at 30° C. for one day, and the solid was separated. The filter cake was then dried under vacuum at 20° C. for 24 h to obtain 0.067 g of solid as crystal form A. Its X-ray powder diffraction pattern and DSC curve are consistent with FIGS. 1-2, respectively.

Example 6 Preparation of Crystal Form A 0.1 g of the compound of formula I was mixed with 4 mL of ethyl acetate to obtain a suspension, which was then stirred at 50° C. for one day, and the solid was separated. The filter cake was then dried under vacuum at 60° C. for 24 h to obtain 0.068 g of solid as crystal form A. Its X-ray powder diffraction pattern and DSC curve are consistent with FIGS. 1-2, respectively.

Example 7 Preparation of Crystal Form A 0.1 g of the compound of formula I was mixed with 5 mL of n-propanol to obtain a suspension, which was then stirred at 22° C. for one day, and the solid was separated. The filter cake was then dried under vacuum at 30° C. for 24 h to obtain 0.075 g of solid as crystal form A. Its X-ray powder diffraction pattern and DSC curve are consistent with FIGS. 1-2, respectively.

Example 8 Preparation of Crystal Form A 0.1 g of the compound of formula I was mixed with 4 mL of acetone to obtain a suspension, which was then stirred at 50° C. for one day, and the solid was separated. The filter cake was then dried under vacuum at 50° C. for 24 h to obtain 0.056 g of solid as crystal form A. Its X-ray powder diffraction pattern and DSC curve are consistent with FIGS. 1-2, respectively.

Example 9 Preparation of Crystal Form A 0.1 g of the compound of formula I was mixed with 5 mL of acetonitrile to obtain a suspension, which was then stirred at 30° C. for seven days, and the solid was separated. The filter cake was then dried under vacuum at 30° C. for 24 h to obtain 0.066 g of solid as crystal form A. Its X-ray powder diffraction pattern and DSC curve are consistent with FIGS. 1-2, respectively.

Example 10 Preparation of Crystal Form A 0.1 g of the compound of formula I was mixed with 1 mL of methanol and 1 mL of ethanol to obtain a suspension, which was then stirred at 15° C. for two days, and the solid was separated. The filter cake was then dried under vacuum at 50° C. for 12 h to obtain 0.064 g of solid as crystal form A. Its X-ray powder diffraction pattern and DSC curve are shown in FIGS. 1-2, respectively.

Example 11 Preparation of Crystal Form A 0.1 g of the compound of formula I was mixed with 0.5 mL of methyl acetate and 1 mL of ethyl acetate to obtain a suspension, which was then stirred at 20° C. for four days, and the solid was separated. The filter cake was then dried under vacuum at 50° C. for 8 h to obtain 0.071 g of solid as crystal form A. Its X-ray powder diffraction pattern and DSC curve are shown in FIGS. 1-2, respectively.

Example 12 Preparation of Crystal Form A 0.1 g of the compound of formula I was mixed with 3 mL of DMSO, stirred at 20° C. to obtain a clear solution after dissolution, added with 5 mL of water, stirred until precipitation, and the solid was separated. The filter cake was then dried under vacuum at 50° C. for 24 h to obtain 0.065 g of solid as crystal form A. Its X-ray powder diffraction pattern and DSC curve are consistent with FIGS. 1-2, respectively.

Example 13 Preparation of Crystal Form A 0.1 g of the compound of formula I was mixed with 2 mL of DMSO, stirred at 25° C. to obtain a clear solution after dissolution, added with 3 mL of ethanol and 5 mL of water, stirred until precipitation, and the solid was separated. The filter cake was then dried under vacuum at 50° C. for 12 h to obtain 0.055 g of solid as crystal form A. Its X-ray powder diffraction pattern and DSC curve are consistent with FIGS. 1-2, respectively.

Example 14 Preparation of Crystal Form A 0.1 g of the compound of formula I was mixed with 4 mL of DMSO, stirred at 30° C. to obtain a clear solution after dissolution, added with 3 mL of ethyl acetate and 10 ml of water, stirred until precipitation, and the solid was separated. The filter cake was then dried under vacuum at 60° C. for 8 h to obtain 0.058 g of solid as crystal form A. Its X-ray powder diffraction pattern and DSC curve are consistent with FIGS. 1-2, respectively.

Example 15 Preparation of Crystal Form A 0.1 g of the compound of formula I was mixed with 1 mL of DMSO, stirred at 50° C. to obtain a clear solution after dissolution, added with 2 mL of acetonitrile, stirred until precipitation, and the solid was separated. The filter cake was then dried under vacuum at 20° C. for 24 h to obtain 0.067 g of solid as crystal form A. Its X-ray powder diffraction pattern and DSC curve are consistent with FIGS. 1-2, respectively.

Example 16 Preparation of Crystal Form A 0.1 g of the compound of formula I was mixed with 1 mL of dichloromethane, stirred at 30° C. to obtain a clear solution after dissolution, added with 1 mL of methanol and 5 mL of n-heptane, stirred until precipitation, and the solid was separated. The filter cake was then dried under vacuum at 40° C. for 12 h to obtain 0.056 g of solid as crystal form A. Its X-ray powder diffraction pattern and DSC curve are consistent with FIGS. 1-2, respectively.

Example 17 Preparation of Crystal Form A 0.1 g of the compound of formula I was mixed with 4 mL of dichloromethane, stirred at 20° C. to obtain a clear solution after dissolution, added with 5 mL of n-heptane, stirred until precipitation, and the solid was separated. The filter cake was then dried under vacuum at 50° C. for 24 h to obtain 0.063 g of solid as crystal form A. Its X-ray powder diffraction pattern and DSC curve are consistent with FIGS. 1-2, respectively.

Example 18 Preparation of Crystal Form A 0.1 g of the compound of formula I was mixed with 2 mL of DMF, stirred at 22° C. to obtain a clear solution after dissolution, added with 2 mL of isopropanol and 5 mL of water, stirred until precipitation, and the solid was separated. The filter cake was then dried under vacuum at 60° C. for 8 h to obtain 0.057 g of solid as crystal form A. Its X-ray powder diffraction pattern and DSC curve are consistent with FIGS. 1-2, respectively.

Example 19 Preparation of Crystal Form A 0.1 g of the compound of formula I was mixed with 1 mL of DMF, stirred at 30° C. to obtain a clear solution after dissolution, added with 5 mL of isopropyl acetate, stirred until precipitation, and the solid was separated. The filter cake was then dried under vacuum at 40° C. for 10 h to obtain 0.055 g of solid as crystal form A. Its X-ray powder diffraction pattern and DSC curve are consistent with FIGS. 1-2, respectively.

Example 20 Preparation of Crystal Form A 0.1 g of the compound of formula I was mixed with 1 mL of DMF, stirred at 50° C. to obtain a clear solution after dissolution, added with 3 mL of acetonitrile, stirred until precipitation, and the solid was separated. The filter cake was then dried under vacuum at 60° C. for 24 h to obtain 0.048 g of solid as crystal form A. Its X-ray powder diffraction pattern and DSC curve are consistent with FIGS. 1-2, respectively.

Example 21 Preparation of Crystal Form A 0.1 g of the compound of formula I was mixed with 1 mL of DMF, stirred at 50° C. to obtain a clear solution after dissolution, added with 5 mL of acetone, stirred until precipitation, and the solid was separated. The filter cake was then dried under vacuum at 60° C. for 8 h to obtain 0.055 g of solid as crystal form A. Its X-ray powder diffraction pattern and DSC curve are consistent with FIGS. 1-2, respectively.

Example 22 Preparation of Crystal Form A 0.1 g of the compound of formula I was mixed with 0.5 mL of DMF, stirred at 40° C. to obtain a clear solution after dissolution, added with 6 mL of acetonitrile and 4 mL of water, stirred until precipitation, and the solid was separated. The filter cake was then dried under vacuum at 60° C. for 12 h to obtain 0.061 g of solid as crystal form A. Its X-ray powder diffraction pattern and DSC curve are consistent with FIGS. 1-2, respectively.

Example 23 Preparation of Crystal Form A 0.1 g of the compound of formula I was mixed with 1 mL of DMF, stirred at 20° C. to obtain a clear solution after dissolution, added with 1 mL of ethanol and 1 mL of water, stirred until precipitation, and the solid was separated. The filter cake was then dried under vacuum at 60° C. for 20 h to obtain 0.063 g of solid as crystal form A. Its X-ray powder diffraction pattern and DSC curve are consistent with FIGS. 1-2, respectively.

Example 24 Preparation of Crystal Form A 0.1 g of the compound of formula I was mixed with 1 mL of DMAC, stirred at 25° C. to obtain a clear solution after dissolution, added with 2 mL of ethanol and 5 mL of water, stirred until precipitation, and the solid was separated. The filter cake was then dried under vacuum at 60° C. for 8 h to obtain 0.065 g of solid as crystal form A. Its X-ray powder diffraction pattern and DSC curve are consistent with FIGS. 1-2, respectively.

Example 25 Preparation of Crystal Form A 0.1 g of the compound of formula I was mixed with 1 mL of DMAC, stirred at 50° C. to obtain a clear solution after dissolution, added with 2 mL of methanol, stirred until precipitation, and the solid was separated. The filter cake was then dried under vacuum at 50° C. for 12 h to obtain 0.067 g of solid as crystal form A. Its X-ray powder diffraction pattern and DSC curve are consistent with FIGS. 1-2, respectively.

Example 26 Preparation of Crystal Form A 0.1 g of the compound of formula I was mixed with 0.6 mL of DMAC, stirred at 20° C. to obtain a clear solution after dissolution, added with 3 mL of ethanol and 7 mL of water, stirred until precipitation, and the solid was separated. The filter cake was then dried under vacuum at 50° C. for 24 h to obtain 0.072 g of solid as crystal form A. Its X-ray powder diffraction pattern and DSC curve are consistent with FIGS. 1-2, respectively.

Example 27 Preparation of Crystal Form A 0.1 g of the compound of formula I was mixed with 3 mL of DMAC, stirred at 30° C. to obtain a clear solution after dissolution, added with 10 mL of water, stirred until precipitation, and the solid was separated. The filter cake was then dried under vacuum at 50° C. for 12 h to obtain 0.062 g of solid as crystal form A. Its X-ray powder diffraction pattern and DSC curve are consistent with FIGS. 1-2, respectively.

Example 28 Preparation of Crystal Form A 0.1 g of the compound of formula I was mixed with 5 mL of n-butanol to obtain a suspension, which was then stirred at 40° C. for one day, and the solid was separated. The filter cake was then dried under vacuum at 60° C. for 24 h to obtain 0.071 g of solid as crystal form A. Its X-ray powder diffraction pattern and DSC curve are consistent with FIGS. 1-2, respectively.

Example 29 Preparation of Crystal Form A 0.1 g of the compound of formula I was mixed with 0.2 mL of n-butanol to obtain a suspension, which was then stirred at 5° C. for seven days, and the solid was separated. The filter cake was then dried under vacuum at 60° C. for 8 h to obtain 0.055 g of solid as crystal form A. Its X-ray powder diffraction pattern and DSC curve are consistent with FIGS. 1-2, respectively.

Example 30 Preparation of Crystal Form A 0.1 g of the compound of formula I was mixed with 1 mL of n-butanol to obtain a suspension, which was then stirred at 15° C. for three days, and the solid was separated. The filter cake was then dried under vacuum at 40° C. for 12 h to obtain 0.058 g of solid as crystal form A. Its X-ray powder diffraction pattern and DSC curve are consistent with FIGS. 1-2, respectively.

Example 31 Preparation of Crystal Form B 0.1 g of the compound of formula I was mixed with 4 mL of 2-butanone to obtain a suspension, which was then stirred at 25° C. for one day, and the solid was separated. The filter cake was then dried under vacuum at 60° C. for 12 h to obtain 0.070 g of solid as crystal form B. Its X-ray powder diffraction pattern and DSC curve are consistent with FIGS. 3-4, respectively.

Figure 3:
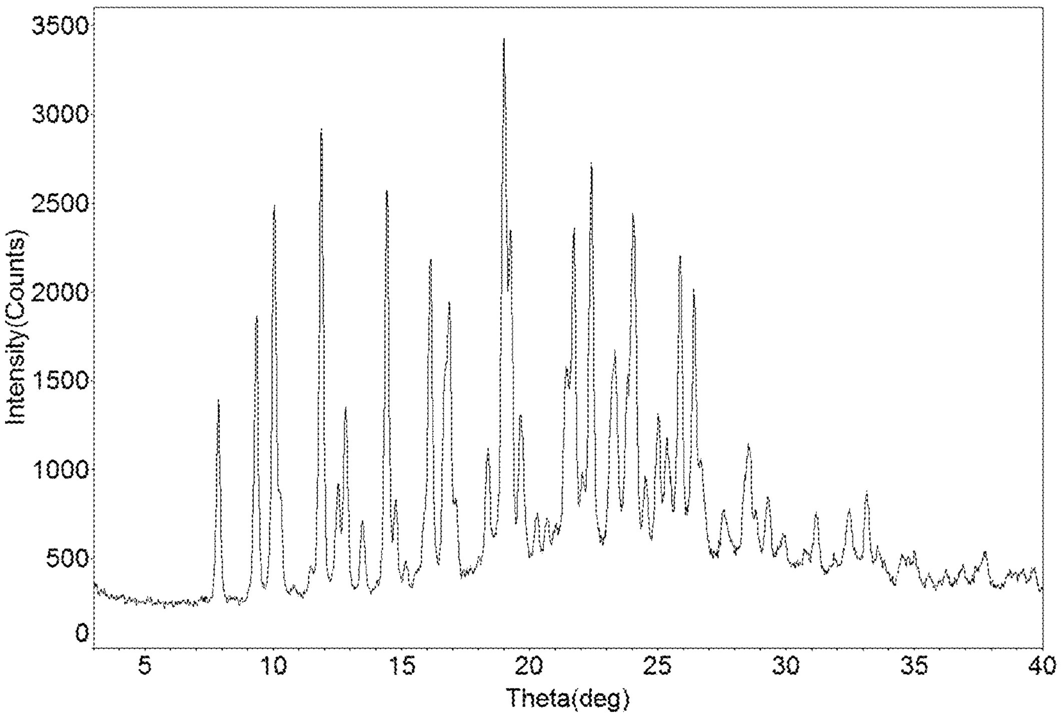
FIG. 3 is the X-ray powder diffraction pattern of the crystal form B prepared in Example 32.
Figure 4:
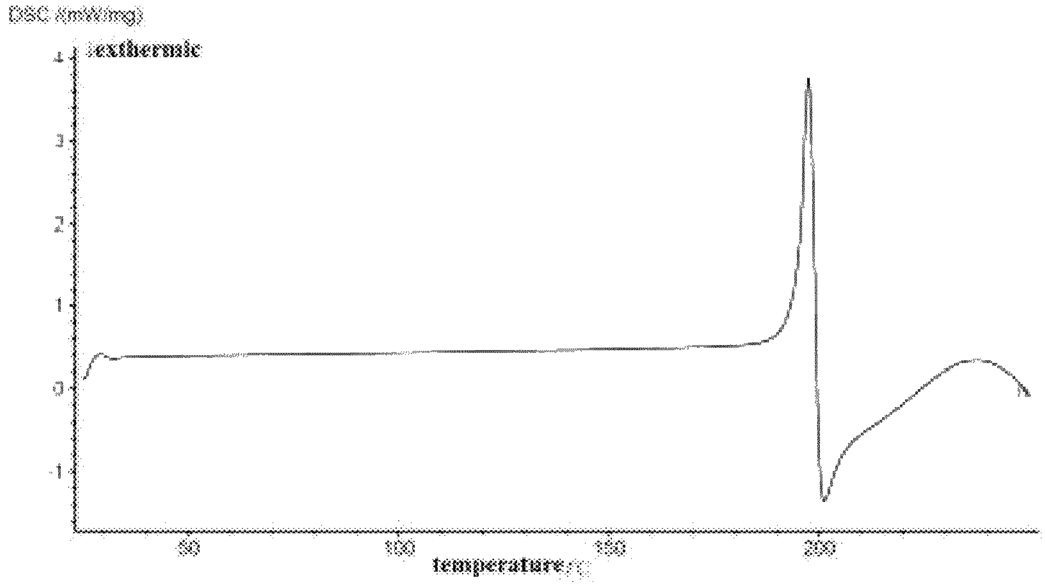
FIG. 4 is the DSC curve of the crystal form B prepared in Example 32.

Example 32 Preparation of Crystal Form B 0.1 g of the compound of formula I was mixed with 5 mL of n-heptane to obtain a suspension, which was then stirred at 5° C. for seven days, and the solid was separated. The filter cake was then dried under vacuum at 50° C. for 24 h to obtain 0.067 g of solid as crystal form B. Its X-ray powder diffraction pattern and DSC curve are shown in FIGS. 3-4, respectively.

Example 33 Preparation of Crystal Form B 0.1 g of the compound of formula I was mixed with 3 mL of butyl acetate to obtain a suspension, which was then stirred at 50° C. for two days, and the solid was separated. The filter cake was then dried under vacuum at 60° C. for 24 h to obtain 0.071 g of solid as crystal form B. Its X-ray powder diffraction pattern and DSC curve are consistent with FIGS. 3-4, respectively.

Example 34 Preparation of Crystal Form B 0.1 g of the compound of formula I was mixed with 2 mL of 1,4-dioxane to obtain a suspension, which was then stirred at 30° C. for three days, and the solid was separated. The filter cake was then dried under vacuum at 40° C. for 8 h to obtain 0.066 g of solid as crystal form B. Its X-ray powder diffraction pattern and DSC curve are consistent with FIGS. 3-4, respectively.

Example 35 Preparation of Crystal Form B 0.1 g of the compound of formula I was mixed with 1 mL of water to obtain a suspension, which was then stirred at 20° C. for one day, and the solid was separated. The filter cake was then dried under vacuum at 60° C. for 24 h to obtain 0.075 g of solid as crystal form B. Its X-ray powder diffraction pattern and DSC curve are consistent with FIGS. 3-4, respectively.

Example 36 Preparation of Crystal Form B 0.1 g of the compound of formula I was mixed with 5 mL of isobutyl acetate to obtain a suspension, which was then stirred at 50° C. for five days, and the solid was separated. The filter cake was then dried under vacuum at 30° C. for 24 h to obtain 0.074 g of solid as crystal form B. Its X-ray powder diffraction pattern and DSC curve are consistent with FIGS. 3-4, respectively.

Example 37 Preparation of Crystal Form B 0.1 g of the compound of formula I was mixed with 0.2 mL of isopropyl acetate to obtain a suspension, which was then stirred at 15° C. for one day, and the solid was separated. The filter cake was then dried under vacuum at 20° C. for 12 h to obtain 0.054 g of solid as crystal form B. Its X-ray powder diffraction pattern and DSC curve are consistent with FIGS. 3-4, respectively.

Example 38 Preparation of Crystal Form B 0.1 g of the compound of formula I was mixed with 0.5 mL of methyl isobutyl ketone to obtain a suspension, which was then stirred at 10° C. for three days, and the solid was separated. The filter cake was then dried under vacuum at 40° C. for 8 h to obtain 0.055 g of solid as crystal form B. Its X-ray powder diffraction pattern and DSC curve are consistent with FIGS. 3-4, respectively.

Example 39 Preparation of Crystal Form B 0.1 g of the compound of formula I was mixed with 0.5 mL of methyl isobutyl ketone and 0.5 mL of 2-butanone to obtain a suspension, which was then stirred at 40° C. for two days, and the solid was separated. The filter cake was then dried under vacuum at 50° C. for 12 h to obtain 0.051 g of solid as crystal form B. Its X-ray powder diffraction pattern and DSC curve are consistent with FIGS. 3-4, respectively.

Example 40 Preparation of Crystal Form B 0.1 g of the compound of formula I was mixed with 1 mL of butyl acetate and 1 mL of isopropyl acetate to obtain a suspension, which was then stirred at 50° C. for one day, and the solid was separated. The filter cake was then dried under vacuum at 60° C. for 8 h to obtain 0.061 g of solid as crystal form B. Its X-ray powder diffraction pattern and DSC curve are consistent with FIGS. 3-4, respectively.

Example 41 Preparation of Crystal Form B 0.1 g of the compound of formula I was mixed with 3 mL of dichloromethane, stirred at 20° C. to obtain a clear solution after dissolution, added with 1 mL of isobutyl acetate and 5 mL of n-heptane, stirred until precipitation, and the solid was separated. The filter cake was then dried under vacuum at 60° C. for 24 h to obtain 0.057 g of solid as crystal form B. Its X-ray powder diffraction pattern and DSC curve are consistent with FIGS. 3-4, respectively.

Example 42 Preparation of Crystal Form B 0.1 g of the compound of formula I was mixed with 1 mL of dichloromethane, stirred at 30° C. to obtain a clear solution after dissolution, added with 1 mL of isobutyl acetate and 1 mL of n-heptane, stirred until precipitation, and the solid was separated. The filter cake was then dried under vacuum at 20° C. for 8 h to obtain 0.055 g of solid as crystal form B. Its X-ray powder diffraction pattern and DSC curve are consistent with FIGS. 3-4, respectively.

Example 43 Preparation of Crystal Form B 0.1 g of the compound of formula I was mixed with 2 mL of dichloromethane, stirred at 25° C. to obtain a clear solution after dissolution, added with 3 mL of isobutyl acetate and 7 mL of n-heptane, stirred until precipitation, and the solid was separated. The filter cake was then dried under vacuum at 40° C. for 12 h to obtain 0.065 g of solid as crystal form B. Its X-ray powder diffraction pattern and DSC curve are consistent with FIGS. 3-4, respectively.

Example 44 Preparation of Crystal Form C 0.1 g of the compound of formula I was mixed with 0.5 mL of DMAC to obtain a suspension, which was then stirred at 50° C. for 24 h, and the solid was separated. The filter cake was then dried under vacuum at 50° C. for 24 h to obtain 0.044 g of solid as crystal form C. Its X-ray powder diffraction pattern and DSC curve are consistent with FIGS. 5-6, respectively.

Example 45 Preparation of Crystal Form C 0.1 g of the compound of formula I was mixed with 0.2 mL of DMAC to obtain a suspension, which was then stirred at 55° C. for 8 h, and the solid was separated. The filter cake was then dried under vacuum at 20° C. for 12 h to obtain 0.041 g of solid as crystal form C. Its X-ray powder diffraction pattern and DSC curve are consistent with FIGS. 5-6, respectively.

Example 46 Preparation of Crystal Form C 0.1 g of the compound of formula I was mixed with 0.3 mL of DMAC to obtain a suspension, which was then stirred at 60° C. for 12 h, and the solid was separated. The filter cake was then dried under vacuum at 60° C. for 8 h to obtain 0.046 g of solid as crystal form C. Its X-ray powder diffraction pattern and DSC curve are consistent with FIGS. 5-6, respectively.

Example 47 Preparation of Crystal Form C 0.1 g of the compound of formula I was mixed with 0.4 mL of DMAC to obtain a suspension, which was then stirred at 70° C. for 24 h, and the solid was separated. The filter cake was then dried under vacuum at 50° C. for 24 h to obtain 0.045 g of solid as crystal form C. Its X-ray powder diffraction pattern and DSC curve are consistent with FIGS. 5-6, respectively.

Figure 5:
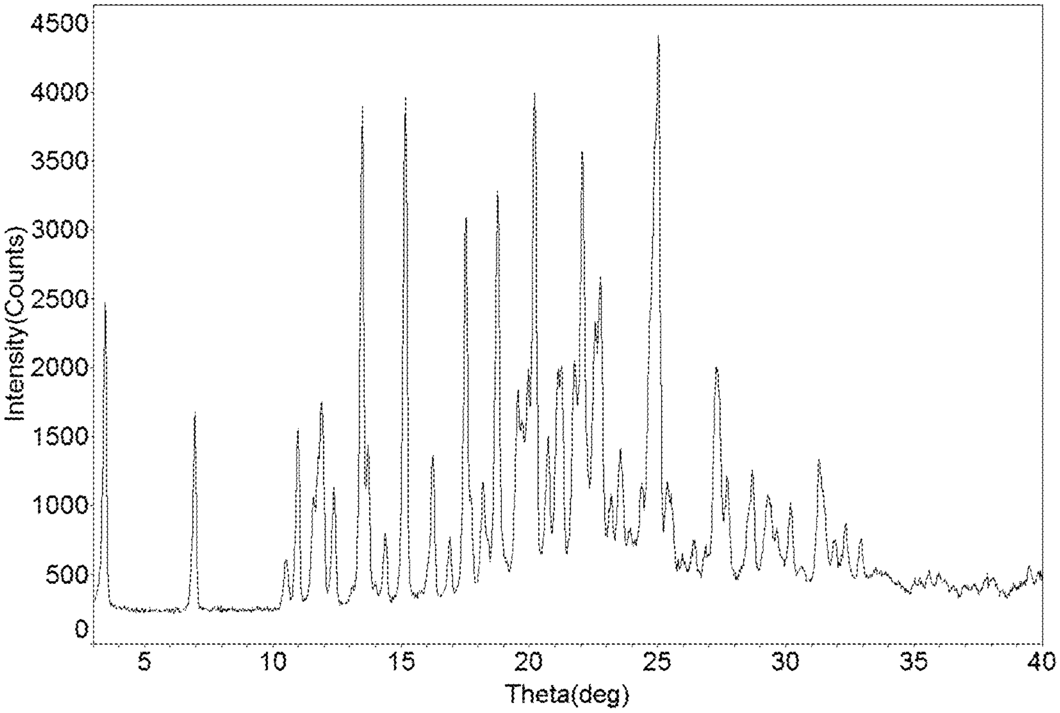
FIG. 5 is the X-ray powder diffraction pattern of the crystal form C prepared in Example 48.
Figure 6:
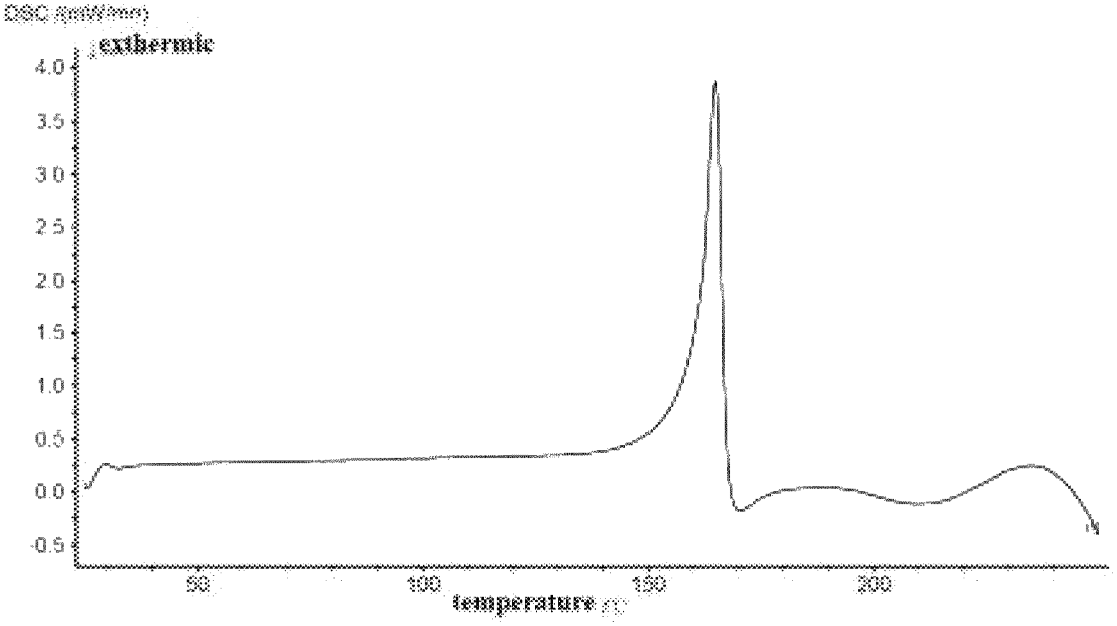
FIG. 6 is the DSC curve of the crystal form C prepared in Example 48.

Example 48 Preparation of Crystal Form C 0.1 g of the compound of formula I was mixed with 1 mL of DMAC, stirred at 60° C. to obtain a clear solution after dissolution, added with 3 mL of n-butanol, stirred until precipitation, and the solid was separated. The filter cake was then dried under vacuum at 60° C. for 8 h to obtain 0.064 g of solid as crystal form C. Its X-ray powder diffraction pattern and DSC curve are shown in FIGS. 5-6, respectively.

Example 49 Preparation of Crystal Form C 0.1 g of the compound of formula I was mixed with 0.6 mL of DMAC, stirred at 70° C. to obtain a clear solution after dissolution, added with 1 mL of isobutyl acetate, stirred until precipitation, and the solid was separated. The filter cake was then dried under vacuum at 30° C. for 12 h to obtain 0.063 g of solid as crystal form C. Its X-ray powder diffraction pattern and DSC curve are consistent with FIGS. 5-6, respectively.

Example 50 Preparation of Crystal Form C 0.1 g of the compound of formula I was mixed with 3 mL of DMAC, stirred at 55° C. to obtain a clear solution after dissolution, added with 5 mL of acetone, stirred until precipitation, and the solid was separated. The filter cake was then dried under vacuum at 20° C. for 24 h to obtain 0.058 g of solid as crystal form C. Its X-ray powder diffraction pattern and DSC curve are consistent with FIGS. 5-6, respectively.

Figure 7:
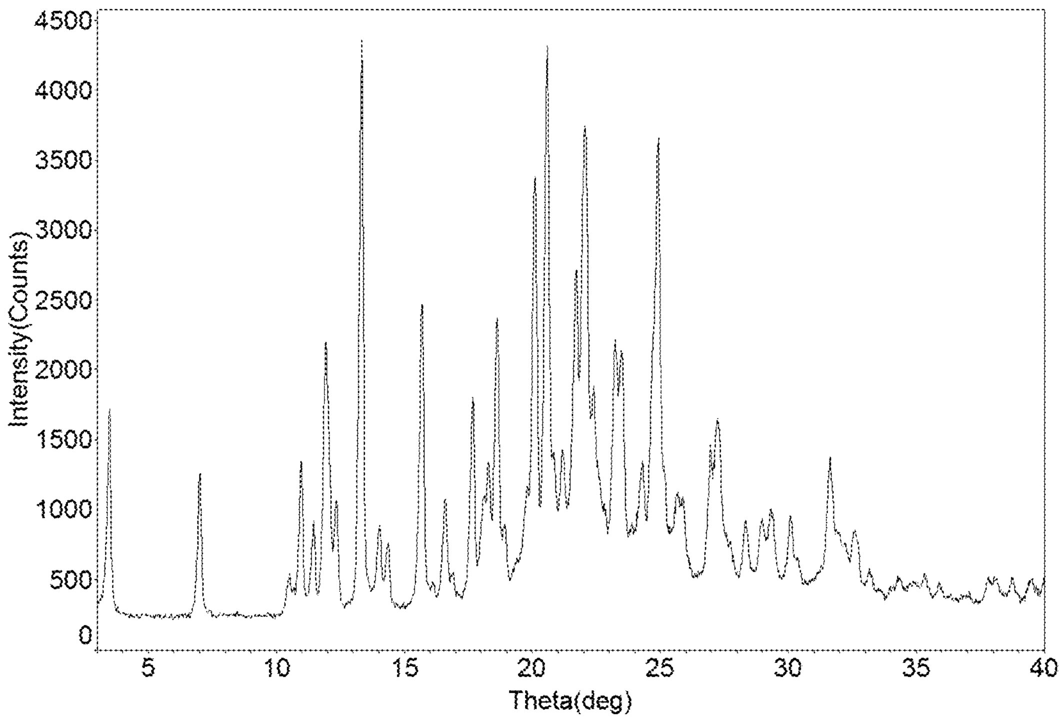
FIG. 7 is the X-ray powder diffraction pattern of the crystal form D prepared in Example 51.
Figure 8:
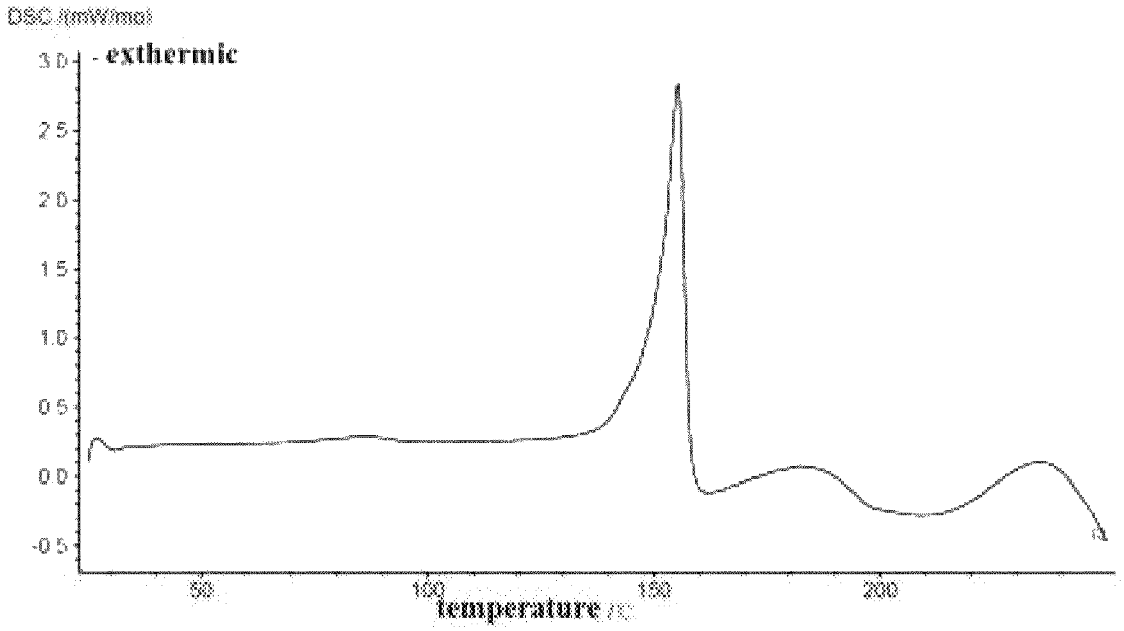
FIG. 8 is the DSC curve of the crystal form D prepared in Example 51.

Example 51 Preparation of Crystal Form D 0.1 g of the compound of formula I was mixed with 3 mL of DMF, stirred at 50° C. to obtain a clear solution after dissolution, added with 2 mL of methanol, cooled down to 20° C., stirred until precipitation, and the solid was separated. The filter cake was then dried under vacuum at 60° C. for 12 h to obtain 0.055 g of solid as crystal form D. Its X-ray powder diffraction pattern and DSC curve are shown in FIGS. 7-8, respectively.

Example 52 Preparation of Crystal Form D 0.1 g of the compound of formula I was mixed with 2 mL of DMF, stirred at 60° C. to obtain a clear solution after dissolution, added with 5 mL of methanol, cooled down to 30° C., stirred until precipitation, and the solid was separated. The filter cake was then dried under vacuum at 20° C. for 24 h to obtain 0.058 g of solid as crystal form D. Its X-ray powder diffraction pattern and DSC curve are consistent with FIGS. 7-8, respectively.

Example 53 Preparation of Crystal Form D 0.1 g of the compound of formula I was mixed with 1 mL of DMF, stirred at 70° C. to obtain a clear solution after dissolution, added with 3 mL of methanol, cooled down to 25° C., stirred until precipitation, and the solid was separated. The filter cake was then dried under vacuum at 40° C. for 8 h to obtain 0.061 g of solid as crystal form D. Its X-ray powder diffraction pattern and DSC curve are consistent with FIGS. 7-8, respectively.

Figure 9:
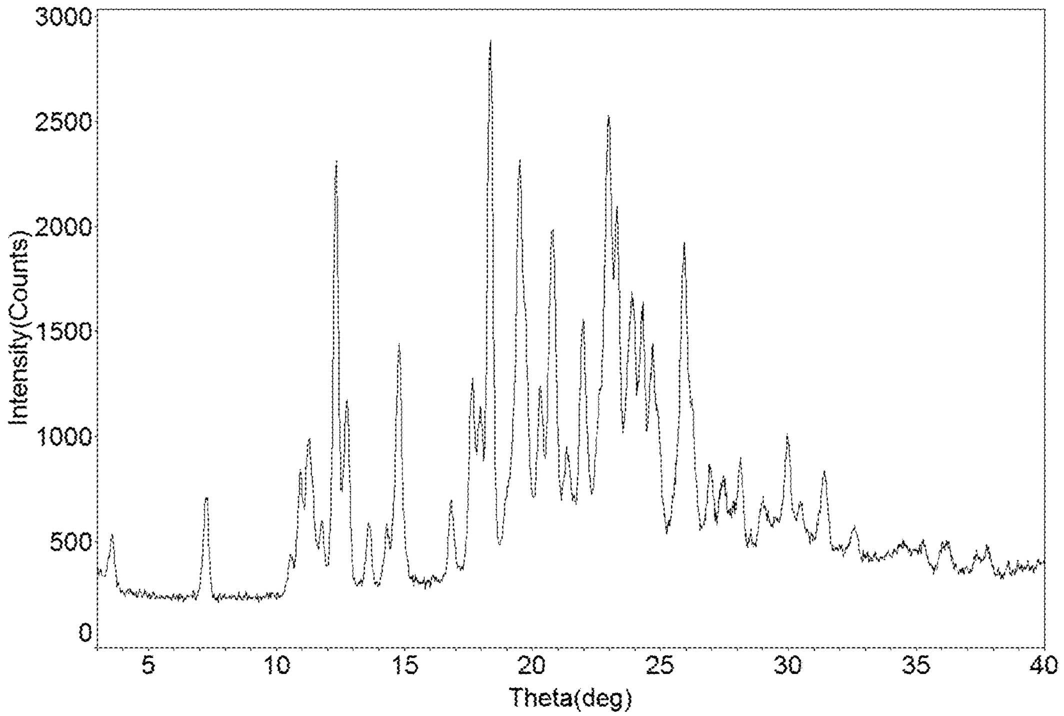
FIG. 9 is the X-ray powder diffraction pattern of the crystal form E prepared in Example 54.
Figure 10:
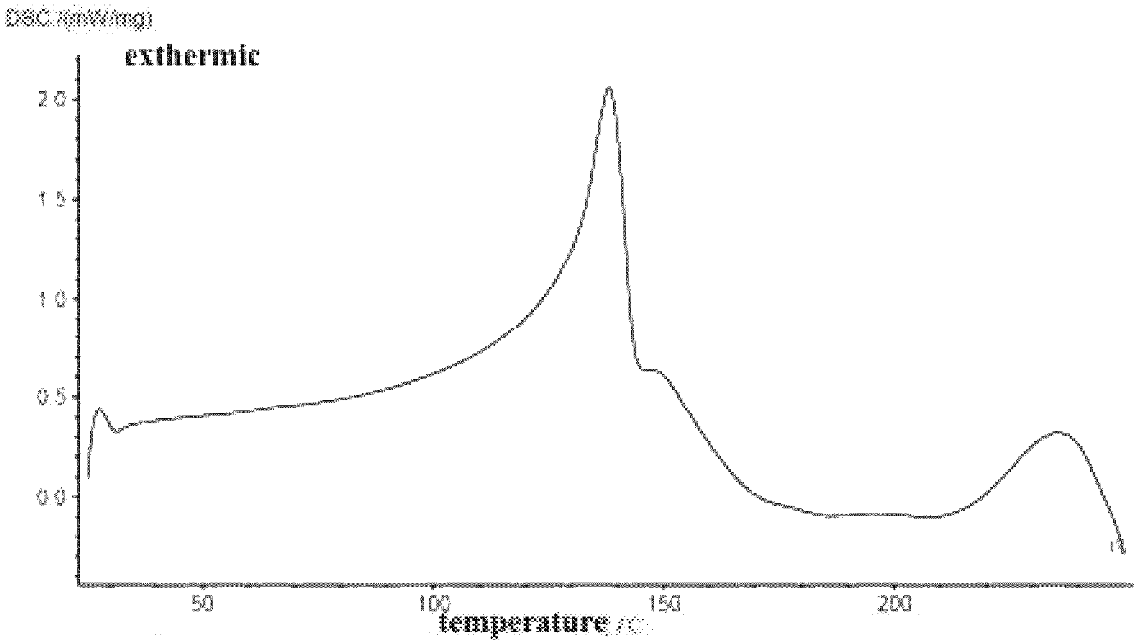
FIG. 10 is the DSC curve of the crystal form E prepared in Example 54.

Example 54 Preparation of Crystal Form E 0.1 g of the compound of formula I was mixed with 1 mL of DMF, stirred at 20° C. to obtain a clear solution after dissolution, added to 2 mL of ethanol and 5 mL of water, stirred until precipitation, and the solid was separated. The filter cake was then dried under vacuum at 60° C. for 8 h to obtain 0.056 g of solid as crystal form E. Its X-ray powder diffraction pattern and DSC curve are shown in FIGS. 9-10, respectively.

Example 55 Preparation of Crystal Form E 0.1 g of the compound of formula I was mixed with 1 mL of DMF, stirred at 22° C. to obtain a clear solution after dissolution, added to 1 mL of acetone and 5 mL of water, stirred until precipitation, and the solid was separated. The filter cake was then dried under vacuum at 50° C. for 12 h to obtain 0.053 g of solid as crystal form E. Its X-ray powder diffraction pattern and DSC curve are consistent with FIGS. 9-10, respectively.

Example 56 Preparation of Crystal Form E 0.1 g of the compound of formula I was mixed with 1 mL of DMF, stirred at 30° C. to obtain a clear solution after dissolution, added to 2 mL of acetonitrile and 7 mL of water, stirred until precipitation, and the solid was separated. The filter cake was then dried under vacuum at 20° C. for 24 h to obtain 0.061 g of solid as crystal form E. Its X-ray powder diffraction pattern and DSC curve are consistent with FIGS. 9-10, respectively.

Example 57 Preparation of Crystal Form E 0.1 g of the compound of formula I was mixed with 0.5 mL of DMF, stirred at 30° C. to obtain a clear solution after dissolution, added to 1 mL acetone and 1 mL water, stirred until precipitation, and the solid was separated. The filter cake was then dried under vacuum at 40° C. for 12 h to obtain 0.062 g of solid as crystal form E. Its X-ray powder diffraction pattern and DSC curve are consistent with FIGS. 9-10, respectively.

Example 58 Preparation of Crystal Form E 0.1 g of the compound of formula I was mixed with 2 mL of DMF, stirred at 25° C. to obtain a clear solution after dissolution, added to 3 mL of acetonitrile and 7 mL of water, stirred until precipitation, and the solid was separated. The filter cake was then dried under vacuum at 60° C. for 24 h to obtain 0.063 g of solid as crystal form E. Its X-ray powder diffraction pattern and DSC curve are consistent with FIGS. 9-10, respectively.

Example 59 Preparation of Crystal Form E 0.1 g of the compound of formula I was mixed with 3 mL of DMAC, stirred at 22° C. to obtain a clear solution after dissolution, added to 2 mL of ethanol and 5 mL of water, stirred until precipitation, and the solid was separated. The filter cake was then dried under vacuum at 60° C. for 10 h to obtain 0.063 g of solid as crystal form E. Its X-ray powder diffraction pattern and DSC curve are consistent with FIGS. 9-10, respectively.

Example 60 Preparation of Crystal Form E 0.1 g of the compound of formula I was mixed with 1 mL of DMAC, stirred at 25° C. to obtain a clear solution after dissolution, added to 3 mL of n-propanol and 6 mL of water, stirred until precipitation, and the solid was separated. The filter cake was then dried under vacuum at 45° C. for 12 h to obtain 0.065 g of solid as crystal form E. Its X-ray powder diffraction pattern and DSC curve are consistent with FIGS. 9-10, respectively.

Example 61 Preparation of Crystal Form E 0.1 g of the compound of formula I was mixed with 0.6 mL of DMAC, stirred at 20° C. to obtain a clear solution after dissolution, added to 3 mL of n-propanol and 7 mL of water, stirred until precipitation, and the solid was separated. The filter cake was then dried under vacuum at 20° C. for 24 h to obtain 0.069 g of solid as crystal form E. Its X-ray powder diffraction pattern and DSC curve are consistent with FIGS. 9-10, respectively.

Example 62 Preparation of Crystal Form E 0.1 g of the compound of formula I was mixed with 2 mL of DMAC, stirred at 30° C. to obtain a clear solution after dissolution, added to 3 mL of n-propanol and 5 mL of water, stirred until precipitation, and the solid was separated. The filter cake was then dried under vacuum at 50° C. for 8 h to obtain 0.066 g of solid as crystal form E. Its X-ray powder diffraction pattern and DSC curve are consistent with FIGS. 9-10, respectively.

Preparation of Amorphous Form of Compound of Formula I

The amorphous form of the compound of formula I was prepared according to Example 5 of WO2017198221A1.

Stability Experiment

The amorphous form of the compound of formula I prepared in Preparation Example, the crystal form A of the compound of formula I prepared in Example 1, the crystal form B of the compound of formula I prepared in Example 32, the crystal form C of the compound of formula I prepared in Example 48, the crystal form D of the compound of formula I prepared in Example 51, and the crystal form E of the compound of formula I prepared in Example 54 were placed in 75% RH, 92.5% RH, 40° C., 60° C. and light for 10 days respectively, and the X-ray powder diffraction pattern and purity of each crystal form were measured. The specific results are shown in Table 6 below:

TABLE 6

| | Crystal form A | Crystal form B | Crystal form C | Crystal form D | Crystal form E | Amorphous form |
|---|---|---|---|---|---|---|
| Day 0 | 99.87 | 99.75 | 99.72 | 99.55 | 99.56 | 95.33 |
| 75% RH for 10 days | 99.85 | 99.75 | 99.71 | 99.54 | 99.56 | 94.93 |
| 92.5% RH for 10 days | 99.83 | 99.73 | 99.68 | 99.54 | 99.54 | 94.83 |
| 40° C. for 10 days | 99.83 | 99.69 | 99.66 | 99.52 | 99.53 | 94.67 |
| 60° C. for 10 days | 99.81 | 99.72 | 99.66 | 99.49 | 99.52 | 94.73 |
| Light for 10 days | 99.87 | 99.73 | 99.70 | 99.53 | 99.55 | 94.97 |

It can be seen from the results in Table 6 that compared with the amorphous form, crystal form A, crystal form B, crystal form C, crystal form D and crystal form E have better stability and higher purity.

Granularity Experiment

The amorphous form of the compound of formula I prepared in Preparation Example, the crystal form A of the compound of formula I prepared in Example 1, the crystal form B of the compound of formula I prepared in Example 32, the crystal form C of the compound of formula I prepared in Example 48, the crystal form D of the compound of formula I prepared in Example 51, and the crystal form E of the compound of formula I prepared in Example 54 were measured for granularity, and the specific results are shown in Table 7 below:

TABLE 7

| | Amorphous form | Crystal form A | Crystal form B | Crystal form C | Crystal form D | Crystal form E |
|---|---|---|---|---|---|---|
| D50 | 2.68 μm | 22.37 μm | 21.98 μm | 21.77 μm | 20.98 μm | 20.98 μm |
| D90 | 22.82 μm | 72.86 μm | 71.56 μm | 70.88 μm | 70.49 μm | 69.99 μm |

The above results indicate that the amorphous form has remarkably small granularity, which is significantly smaller than that of the crystal forms A, B, C, D and E (wherein D50 is 2.68 μm, not exceeding 13% of the crystal forms of the present disclosure; and D90 is 22.82 μm, not exceeding 33% of the crystal forms of the present disclosure).

Fluidity Test

The amorphous form of the compound of formula I prepared in Preparation Example, the crystal form A of the compound of formula I prepared in Example 1, the crystal form B of the compound of formula I prepared in Example 32, the crystal form C of the compound of formula I prepared in Example 48, the crystal form D of the compound of formula I prepared in Example 51, and the crystal form E of the compound of formula I prepared in Example 54 were measured for angle of repose, and the specific results are shown in Table 8 below:

TABLE 8

| | Amorphous form | Crystal form A | Crystal form B | Crystal form C | Crystal form D | Crystal form E |
|---|---|---|---|---|---|---|
| 1 | 43.3° | 33.4° | 34.6° | 34.2° | 35.6° | 35.5° |
| 2 | 42.6° | 31.8° | 35.7° | 35.4° | 36.2° | 36.1° |
| 3 | 41.9° | 33.7° | 35.2° | 33.9° | 35.1° | 35.9° |

The above results indicate that the angle of repose of the amorphous form is significantly larger than that of the crystal forms A, B, C, D and E, showing that the crystal forms A, B, C, D and E are significantly better than the amorphous form in terms of fluidity Hygroscopicity Test The amorphous form of the compound of formula I prepared in Preparation Example, the crystal form A of the compound of formula I prepared in Example 1, the crystal form B of the compound of formula I prepared in Example 32, the crystal form C of the compound of formula I prepared in Example 48, the crystal form D of the compound of formula I prepared in Example 51, and the crystal form E of the compound of formula I prepared in Example 54 were placed in an environment of 75% RH and 25° C. for 24 h and then weighed to calculate the hygroscopicity, respectively. The specific results are shown in Table 9 below:

TABLE 9

| | Amorphous form | Crystal form A | Crystal form B | Crystal form C | Crystal form D | Crystal form E |
|---|---|---|---|---|---|---|
| Hygroscopicity | 0.52% | 0.10% | 0.12% | 0.15% | 0.16% | 0.20% |

The above results indicate that the hygroscopicity of the amorphous form is significantly greater than that of the crystal forms A, B, C, D and E, showing that the crystal forms A, B, C, D and E are significantly better than the amorphous form in terms of hygroscopicity.

Those skilled in the art can understand that the meaning or intended protection scope of the numerical value or numerical endpoint involved in the embodiments of the present disclosure is not limited to the number itself, and includes those allowable error ranges that have been widely accepted in the art, such as experimental error, measurement error, statistical error, random error, etc., and these error ranges are all included in the scope of the present disclosure.

It will be clear to those skilled in the art that many modifications and variations of the present disclosure can be made without departing from its spirit and scope. The specific embodiments described herein are provided by way of example only, and are not meant to be limited in any way. The true scope and spirit of the present disclosure are shown by the appended claims, and the description and examples are only exemplary.

The invention claimed is:

1. A crystal form A of a compound of formula I,

Formula I

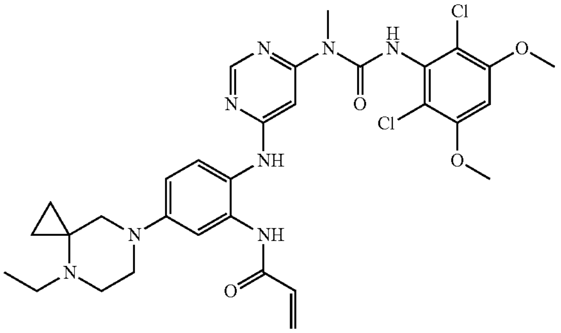

wherein its X-ray powder diffraction pattern with Cu-Kα radiation shows characteristic peaks at 2θ of 7.3±0.2°, 8.4±0.2°, 9.7±0.2°, 12.4±0.2°, 16.7±0.2°, and 19.5±0.2° in degrees.

2. The crystal form A according to claim 1, wherein its X-ray powder diffraction pattern with Cu-Kα radiation further shows characteristic peaks at 2θ of 5.3±0.2°, 12.0±0.2°, 15.1±0.2°, 15.4±0.2°, 16.3±0.2°, 17.1±0.2°, 17.9±0.2°, 18.9±0.2°, 21.1±0.2°, 21.7±0.2°, 22.7±0.2°, 23.1±0.2°, 23.5±0.2°, 24.8±0.2°, 25.4±0.2°, 25.8±0.2°, 26.3±0.2°, 27.1±0.2°, 27.7±0.2°, 28.2±0.2°, 28.6±0.2°, 29.0±0.2°, 30.9±0.2°, 31.5±0.2°, 32.7±0.2°, 34.1±0.2°, 35.9±0.2, and 38.1±0.2° in degrees.

3. A method for preparing the crystal form A according to claim 1, which is any one selected from the group consisting of:

method (1), comprising steps of mixing the compound of formula I with an organic solvent to obtain a suspension, stirring the suspension at 5-50° C. for 1-7 days, separating solid, and drying the solid under vacuum at 20-60° C. for 8-24 h to obtain the crystal form A, wherein the organic solvent is which is any one selected from the group consisting of $C_1$-$C_3$ alcohol, methyl acetate, ethyl acetate, acetone, acetonitrile, and a mixture thereof;

method (2), comprising steps of mixing the compound of formula I with DMSO or dichloromethane, stirring at 20-50° C. to obtain a clear solution after dissolution, adding a poor solvent, stirring until precipitation, separating solid, and drying the solid under vacuum at 20-60° C. for 8-24 h to obtain the crystal form A, wherein the poor solvent is which is any one selected from the group consisting of $C_1$-$C_4$ alcohol, methyl acetate, ethyl acetate, butyl acetate, isopropyl acetate, acetone, acetonitrile, water, an alkane, and a mixture thereof;

method (3), comprising steps of mixing the compound of formula I with DMF, stirring at 20-50° C. to obtain a clear solution after dissolution, adding a poor solvent, stirring until precipitation, separating solid, and drying the solid under vacuum at 20-60° C. for 8-24 h to obtain the crystal form A;

method (4), comprising steps of mixing the compound of formula I with DMAC, stirring at 20-50° C. to obtain a clear solution after dissolution, adding a poor solvent, stirring until precipitation, separating solid, and drying the solid under vacuum at 20-60° C. for 8-24 h to obtain the crystal form A, wherein a weight-volume ratio of the compound of formula I to DMAC is 1:6-1:30 (g/mL); and method (5), comprising steps of mixing the compound of formula I with n-butanol to obtain a suspension, stirring the suspension at 5-40° C. for 1-7 days, separating solid, and drying the solid under vacuum at 20-60° C. for 8-24 h to obtain the crystal form A.

4. A pharmaceutical composition, comprising a therapeutically effective amount of the crystal form A according to claim 1.

5. A method of treating a disease of cancer, comprising administering the crystal form A according to claim 1 to a subject in need thereof, wherein the disease is selected from the group consisting of non-small cell lung cancer, gastric cancer, multiple myeloma, liver cancer, and cholangiocarcinoma.

6. The method according to claim 3, wherein, the $C_1$-$C_3$ alcohol in method (1) is any one selected from the group consisting of methanol, ethanol, n-propanol and isopropanol.

7. The method according to claim 3, wherein, a weight-volume ratio of the compound of formula I to the organic solvent in method (1) is 1:2-1:50 (g/mL).

8. The method according to claim 3, wherein, the $C_1$-$C_4$ alcohol in method (2) is which is any one selected from the group consisting of methanol, ethanol and isopropanol, and the alkane is which is any one selected from the group consisting of n-heptane, n-hexane and cyclohexane.

9. The method according to claim 3, wherein, a weight-volume ratio of the compound of formula I to DMSO or dichloromethane in method (2) is 1:10-1:40 (g/mL).

10. The method according to claim 3, wherein, a weight-volume ratio of the compound of formula I to the poor solvent in method (2) is 1:20-1:130 (g/mL).

11. The method according to claim 3, wherein, the poor solvent in method (3) is which is any one selected from the group consisting of $C_2$-$C_4$ alcohol, isopropyl acetate, acetone, acetonitrile, water, and a mixture thereof.

12. The method according to claim 3, wherein, the $C_2$-$C_4$ alcohol in method (3) is ethanol or isopropanol.

13. The method according to claim 3, wherein, a weight-volume ratio of the compound of formula I to DMF in method (3) is 1:5-1:20 (g/mL).

14. The method according to claim 3, wherein, a weight-volume ratio of the compound of formula I to the poor solvent in method (3) is 1:20-1:100 (g/mL).

15. The method according to claim 3, wherein, the poor solvent in method (4) is which is any one selected from the group consisting of $C_1$-$C_4$ alcohol, water, and a mixture thereof.

16. The method according to claim 3, wherein, the $C_1$-$C_4$ alcohol in method (4) is which is any one selected from the group consisting of methanol, ethanol and isopropanol.

17. The method according to claim 3, wherein, a weight-volume ratio of the compound of formula I to the poor solvent in method (4) is 1:20-1:100 (g/mL).

18. The method according to claim 3, wherein, a weight-volume ratio of the compound of formula I to n-butanol in method (5) is 1:2-1:50 (g/mL).

19. The method according to claim 5, wherein the disease is liver cancer or cholangiocarcinoma.

* * * * *